United States Patent
Collier et al.

(10) Patent No.: US 7,691,806 B2
(45) Date of Patent: *Apr. 6, 2010

(54) REPEAT SEQUENCE PROTEIN POLYMER ACTIVE AGENT CONGJUGATES, METHODS AND USES

(75) Inventors: Katherine D. Collier, Redwood City, CA (US); William A. Cuevas, San Francisco, CA (US); Manoj Kumar, Fremont, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/351,712

(22) Filed: Feb. 10, 2006

(65) Prior Publication Data

US 2006/0153791 A1    Jul. 13, 2006

Related U.S. Application Data

(63) Continuation of application No. 10/845,936, filed on May 14, 2004, now abandoned.

(60) Provisional application No. 60/470,464, filed on May 14, 2003.

(51) Int. Cl.
*A61K 38/00* (2006.01)
*C07K 14/00* (2006.01)
*C07K 17/00* (2006.01)
*A23J 1/00* (2006.01)
*C07K 16/00* (2006.01)
*C07K 1/00* (2006.01)
*A61K 51/00* (2006.01)

(52) U.S. Cl. .......................... 514/2; 530/350; 530/412; 530/427; 424/1.69

(58) Field of Classification Search .............. 514/2
See application file for complete search history.

(56) References Cited

U.S. PATENT DOCUMENTS

| | | | |
|---|---|---|---|
| 5,243,038 | A | 9/1993 | Ferrari et al. |
| 5,412,074 | A | 5/1995 | Jones et al. |
| 5,626,853 | A | 5/1997 | Bara et al. |
| 5,627,148 | A | 5/1997 | Dubief et al. |
| 5,679,543 | A | 10/1997 | Lawlis |
| 6,004,444 | A | 12/1999 | Aksay et al. |
| 6,034,220 | A | 3/2000 | Stedronsky |
| 6,140,072 | A | 10/2000 | Ferrari et al. |
| 6,153,602 | A | 11/2000 | Dubief et al. |
| 6,184,348 | B1 | 2/2001 | Ferrari et al. |
| 6,228,248 | B1 | 5/2001 | Aksay et al. |
| 6,355,776 | B1 | 3/2002 | Ferrari et al. |
| 6,358,501 | B1 | 3/2002 | Dietz et al. |
| 6,365,661 | B1 | 4/2002 | Fischer et al. |
| 6,365,877 | B1 | 4/2002 | Chen et al. |
| 6,368,606 | B1 | 4/2002 | Dubief et al. |
| 2001/0006664 | A1 | 7/2001 | Ensley |
| 2001/0013294 | A1 | 8/2001 | Bruno et al. |
| 2001/0027570 | A1 | 10/2001 | Blees |
| 2002/0064539 | A1 | 5/2002 | Philippe et al. |

FOREIGN PATENT DOCUMENTS

| | | |
|---|---|---|
| EP | 0 540 357 A2 | 5/1993 |
| EP | 0 699 431 A1 | 3/1996 |
| WO | 9523611 A1 | 9/1995 |
| WO | WO 00/35993 | 6/2000 |
| WO | WO 01/46213 A2 | 6/2001 |
| WO | WO 01/87825 A1 | 11/2001 |
| WO | 03099465 A1 | 12/2003 |
| WO | 2004080426 A2 | 9/2004 |

OTHER PUBLICATIONS

Gotoh et al, "Synthesis of poly(ethylene glycol)-silk fibroin conjugates and surface interaction between L-929 cells and the conjugates" Biomaterials, Elsevier Science Publishers BV., Barking, GB, vol. 18, No. 3, pp. 267-271, Feb. 1, 1997.
Kumar et al, "Designer Protein-Based Performance Materials" Biomacromolecules, Sep. 2006 American Chemical Society US, vol. 7, No. 9, pp. 2543-2551, Sep. 2006.
Meyer et al "Targeting a Genetically Engineered Elastin-like Polypeptide to Solid Tumors by Local Hyperthermia" Cancer Research, vol. 61, No. 4, pp. 1548-1554, Feb. 15, 2001.
Supplementary European search report dated Jul. 8, 2009 pertaining to European application No. 04752348.5 filed May 14, 2004.
Deming, Facile synthesis of block copolypeptides of defined architecture, Nature, vol. 390, Nov. 27, 1997, pp. 386-389.
Fan, et al., Rapid prototyping of patterned functional nanostructures, Nature, vol. 405, May 4, 2000, pp. 56-60.
Brott et al., Ultrafast holographic nanopattering of biocatalytically formed silica, Nature, vol. 413, Sep. 20, 2001, pp. 291-293.
Huo et al., Generalized synthesis of periodic surfactant/Inorganic composite materials, Nature, vol. 368, Mar. 24, 1994, pp. 317-321.
Zhou et al., Efficient Catalysis of Polysiloxane Synthesis by Silicatein Requires Specific Hodroxy and Imidazole Functionalities, Agnew. Chem. Inst., Ed. 1999, 38, No. 6, pp. 779-782.
Gosline et al., Elastic proteins; biological roles and mechanical properties The Royal Society, Feb. 28, 2002, pp. 121-132.
Kroger et al., Polycationic Peptides from Diatom Biosilica That Direct Silica Nanosphere Formation, Science, vol. 286, Nov. 5, 1999, pp. 1129-1132.
Naik et al., Silica-Precipitating Peptides Isolated from a Combinatorial Phage Display Peptide Library, Journal of Nano science and Nanotechnology, 2002, vol. 2 No. 1, pp. 95-100.
Kroger et al., Silica-precipitating Peptides from Diatoms, The Chemical Structure of Silaffin-1A From Cylindrotheca Fusiformis, J. Biol. Chem., vol. 276, Issue 28, 26066-26070, Jul. 13, 2001, pp. 1-12.
Mizutani et al. Silicic Acid Polymerization Catalyzed by Amines and Polyamines, Bull, Chem. Soc. Jpn., 71, 2017-2001 (1998).
Mizutani et al., Silicic Acid Polymerization Catalyzed by Amines and Polyamines, Chemistry Letters, 1998 pp. 133-134.

(Continued)

*Primary Examiner*—Maury Audet
(74) *Attorney, Agent, or Firm*—Dinsmore & Shohl LLP

(57) ABSTRACT

Biomolecular conjugates are provided which comprise the conjugation product of a repeat sequence protein polymer and at least one active agent. Additional aspects provide methods for their manufacture and various industrial and consumer applications.

18 Claims, No Drawings

OTHER PUBLICATIONS

Hartgerink et al., Peptide-amphiphile nanofibers: A versitile scaffold for the preparation of self-assembling materials, PNAS, Apr. 16, 2002, vol. 99, No. 8 pp. 5133-5138.

Zhang, Emerging biological materials through molecular self-assembly, Elsevier, Biotechnology Advantages 20 (2002) pp. 321-339.

Wong et al., Assembly of Nanoparticles ino Holly Spheres Using Block Copolypeptides, Nano Letters, vol. O, No. 0, pp. A-E; 2002.

Naik et al., Silica-Precipitating Peptides Isolated from a Combinatorial Phage Display Peptide Library, Journal of Nanoscience and Nanotechnology, 2002, vol. 2, No. 1, pp. 95-100.

Arkles, Commercial Applications of Sol-Gel-Derived Hybrid Materials, Mrs. Bulletin, May 2001, pp. 402-408.

Sarikaya, Biometrics: Materials fabrication through biology, PNAS, Dec. 7, 1999. vol. 96, No. 25, pp. 14183-14185.

Coradin et al., Biogenic Silica Patterning: Simple Chemistry of Subtle Biology? ChemBioChem 2003, 3, pp. 1-9.

```
                            SEQUENCE LISTING

<160> NUMBER OF SEQ ID NOS: 37

<210> SEQ ID NO 1
<211> LENGTH: 6
<212> TYPE: PRT
<213> ORGANISM: unknown
<220> FEATURE:
<223> OTHER INFORMATION: silk fibroin repeat sequence

<400> SEQUENCE: 1

Ser Gly Ala Gly Ala Gly
1               5

<210> SEQ ID NO 2
<211> LENGTH: 53
<212> TYPE: PRT
<213> ORGANISM: unknown
<220> FEATURE:
<223> OTHER INFORMATION: silk fibroin peptide repeat sequence

<400> SEQUENCE: 2

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Ala Gly Tyr
    50

<210> SEQ ID NO 3
<211> LENGTH: 5
<212> TYPE: PRT
<213> ORGANISM: unknown
<220> FEATURE:
<223> OTHER INFORMATION: elastin peptide sequence

<400> SEQUENCE: 3

Gly Val Gly Val Pro
1               5
```

-continued

```
<210> SEQ ID NO 4
<211> LENGTH: 10
<212> TYPE: PRT
<213> ORGANISM: unknown
<220> FEATURE:
<223> OTHER INFORMATION: repeat sequence protein polymer
<220> FEATURE:
<221> NAME/KEY: misc_feature
<222> LOCATION: (10)..(10)
<223> OTHER INFORMATION: Xaa can be any naturally occurring amino acid

<400> SEQUENCE: 4

Gly Gly Phe Gly Gly Met Gly Gly Gly Xaa
1               5                   10

<210> SEQ ID NO 5
<211> LENGTH: 5
<212> TYPE: PRT
<213> ORGANISM: unknown
<220> FEATURE:
<223> OTHER INFORMATION: repeat sequence protein polymer

<400> SEQUENCE: 5

Gly Pro Gly Gly Gly
1               5

<210> SEQ ID NO 6
<211> LENGTH: 6
<212> TYPE: PRT
<213> ORGANISM: unknown
<220> FEATURE:
<223> OTHER INFORMATION: artificial repeat sequence

<400> SEQUENCE: 6

Pro Gly Gln Gly Gln Gln
1               5

<210> SEQ ID NO 7
<211> LENGTH: 9
<212> TYPE: PRT
<213> ORGANISM: unknown
<220> FEATURE:
<223> OTHER INFORMATION: artificial repeat sequence

<400> SEQUENCE: 7

Gly Tyr Tyr Pro Thr Ser Pro Gln Gln
1               5

<210> SEQ ID NO 8
<211> LENGTH: 3
<212> TYPE: PRT
<213> ORGANISM: wheat

<400> SEQUENCE: 8

Gly Gln Gln
1

<210> SEQ ID NO 9
<211> LENGTH: 28
<212> TYPE: PRT
<213> ORGANISM: unknown
<220> FEATURE:
<223> OTHER INFORMATION: artificial repeat sequence

<400> SEQUENCE: 9

Pro Pro Ala Lys Val Pro Glu Val Pro Lys Lys Pro Val Pro Glu Glu
1               5                   10                  15
```

```
Lys Val Pro Val Pro Val Pro Lys Lys Pro Glu Ala
            20                  25

<210> SEQ ID NO 10
<211> LENGTH: 12
<212> TYPE: PRT
<213> ORGANISM: human

<400> SEQUENCE: 10

Ser Pro Pro Pro Pro Ser Pro Lys Tyr Val Tyr Lys
1               5                   10

<210> SEQ ID NO 11
<211> LENGTH: 4
<212> TYPE: PRT
<213> ORGANISM: tomato

<400> SEQUENCE: 11

Arg Gly Asp Ser
1

<210> SEQ ID NO 12
<211> LENGTH: 5
<212> TYPE: PRT
<213> ORGANISM: unknown
<220> FEATURE:
<223> OTHER INFORMATION: artificial repeat sequence

<400> SEQUENCE: 12

Pro Gln Gln Pro Tyr
1               5

<210> SEQ ID NO 13
<211> LENGTH: 5
<212> TYPE: PRT
<213> ORGANISM: unknown
<220> FEATURE:
<223> OTHER INFORMATION: artificial repeat sequence

<400> SEQUENCE: 13

Pro Thr Thr Thr Lys
1               5

<210> SEQ ID NO 14
<211> LENGTH: 8
<212> TYPE: PRT
<213> ORGANISM: unknown
<220> FEATURE:
<223> OTHER INFORMATION: artificial repeat sequence

<400> SEQUENCE: 14

Ala Gly Tyr Gly Ser Thr Gly Thr
1               5

<210> SEQ ID NO 15
<211> LENGTH: 8
<212> TYPE: PRT
<213> ORGANISM: unknown
<220> FEATURE:
<223> OTHER INFORMATION: artificial repeat sequence

<400> SEQUENCE: 15

Tyr Gly Gly Ser Ser Gly Gly Gly
1               5
```

```
<210> SEQ ID NO 16
<211> LENGTH: 5
<212> TYPE: PRT
<213> ORGANISM: unknown
<220> FEATURE:
<223> OTHER INFORMATION: artificial repeat sequence

<400> SEQUENCE: 16

Phe Gly Gly Gly Ser
1               5

<210> SEQ ID NO 17
<211> LENGTH: 6
<212> TYPE: PRT
<213> ORGANISM: unknown
<220> FEATURE:
<223> OTHER INFORMATION: artificial repeat sequence

<400> SEQUENCE: 17

Thr Thr Thr Pro Asp Val
1               5

<210> SEQ ID NO 18
<211> LENGTH: 7
<212> TYPE: PRT
<213> ORGANISM: unknown
<220> FEATURE:
<223> OTHER INFORMATION: artificial repeat sequence

<400> SEQUENCE: 18

Tyr Ser Pro Thr Ser Pro Ser
1               5

<210> SEQ ID NO 19
<211> LENGTH: 780
<212> TYPE: PRT
<213> ORGANISM: unknown
<220> FEATURE:
<223> OTHER INFORMATION: silk and elastin peptide repeats

<400> SEQUENCE: 19

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Lys Gly Val Pro
                20                  25                  30

Gly Val Gly Pro Gly Val Gly Pro Gly Val Gly Pro Gly Val Gly Pro
            35                  40                  45

Gly Ala Gly Ala Gly Ser Gly Ala Gly Ala Gly Ser Gly Ala Gly Ala
        50                  55                  60

Gly Ser Gly Ala Gly Ala Gly Ser Gly Val Gly Val Pro Gly Val Gly
65                  70                  75                  80

Val Pro Gly Val Gly Val Pro Gly Lys Gly Val Pro Gly Val Gly Pro
                85                  90                  95

Gly Val Gly Pro Gly Val Gly Pro Gly Val Gly Pro Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Val Gly Val Pro Gly Val Gly Val Pro Gly Val
        130                 135                 140

Gly Val Pro Gly Lys Gly Val Pro Gly Val Gly Pro Gly Val Gly Pro
145                 150                 155                 160

Gly Val Gly Pro Gly Val Gly Pro Gly Ala Gly Ala Gly Ser Gly Ala
```

-continued

```
                165                 170                 175
Gly Ala Gly Ser Gly Ala Gly Ala Gly Ser Gly Ala Gly Ser
            180                 185                 190
Gly Val Gly Val Pro Gly Val Gly Val Pro Gly Val Gly Val Pro Gly
        195                 200                 205
Lys Gly Val Pro Gly Val Gly Pro Gly Val Gly Pro Gly Val Gly Pro
210                 215                 220
Gly Val Gly Pro Gly Ala Gly Ala Gly Ser Gly Ala Gly Ala Gly Ser
225                 230                 235                 240
Gly Ala Gly Ala Gly Ser Gly Ala Gly Ala Gly Ser Gly Val Gly Val
            245                 250                 255
Pro Gly Val Gly Val Pro Gly Val Gly Val Pro Gly Lys Gly Val Pro
                260                 265                 270
Gly Val Gly Pro Gly Val Gly Pro Gly Val Gly Pro Gly Val Gly Pro
            275                 280                 285
Gly Ala Gly Ala Gly Ser Gly Ala Gly Ala Gly Ser Gly Ala Gly Ala
        290                 295                 300
Gly Ser Gly Ala Gly Ala Gly Ser Gly Val Gly Val Pro Gly Val Gly
305                 310                 315                 320
Val Pro Gly Val Gly Val Pro Gly Lys Gly Val Pro Gly Val Gly Pro
            325                 330                 335
Gly Val Gly Pro Gly Val Gly Pro Gly Val Gly Pro Gly Ala Gly Ala
        340                 345                 350
Gly Ser Gly Ala Gly Ala Gly Ser Gly Ala Gly Ala Gly Ser Gly Ala
    355                 360                 365
Gly Ala Gly Ser Gly Val Gly Val Pro Gly Val Gly Val Pro Gly Val
370                 375                 380
Gly Val Pro Gly Lys Gly Val Pro Gly Val Gly Pro Gly Val Gly Pro
385                 390                 395                 400
Gly Val Gly Pro Gly Val Gly Pro Gly Ala Gly Ala Gly Ser Gly Ala
                405                 410                 415
Gly Ala Gly Ser Gly Ala Gly Ala Gly Ser Gly Ala Gly Ala Gly Ser
            420                 425                 430
Gly Val Gly Val Pro Gly Val Gly Val Pro Gly Val Gly Val Pro Gly
        435                 440                 445
Lys Gly Val Pro Gly Val Gly Pro Gly Val Gly Pro Gly Val Gly Pro
    450                 455                 460
Gly Val Gly Pro Gly Ala Gly Ala Gly Ser Gly Ala Gly Ala Gly Ser
465                 470                 475                 480
Gly Ala Gly Ala Gly Ser Gly Ala Gly Ala Gly Ser Gly Val Gly Val
            485                 490                 495
Pro Gly Val Gly Val Pro Gly Val Gly Val Pro Gly Lys Gly Val Pro
                500                 505                 510
Gly Val Gly Pro Gly Val Gly Pro Gly Val Gly Pro Gly Val Gly Pro
            515                 520                 525
Gly Ala Gly Ala Gly Ser Gly Ala Gly Ala Gly Ser Gly Ala Gly Ala
        530                 535                 540
Gly Ser Gly Ala Gly Ala Gly Ser Gly Val Gly Val Pro Gly Val Gly
545                 550                 555                 560
Val Pro Gly Val Gly Val Pro Gly Lys Gly Val Pro Gly Val Gly Pro
            565                 570                 575
Gly Val Gly Pro Gly Val Gly Pro Gly Val Gly Pro Gly Ala Gly Ala
        580                 585                 590
```

-continued

```
Gly Ser Gly Ala Gly Ala Gly Ser Gly Ala Gly Ala Gly Ser Gly Ala
            595                 600                 605
Gly Ala Gly Ser Gly Val Gly Val Pro Gly Val Gly Val Pro Gly Val
        610                 615                 620
Gly Val Pro Gly Lys Gly Val Pro Gly Val Gly Pro Gly Val Gly Pro
625                 630                 635                 640
Gly Val Gly Pro Gly Val Gly Pro Gly Ala Gly Ala Gly Ser Gly Ala
            645                 650                 655
Gly Ala Gly Ser Gly Ala Gly Ala Gly Ser Gly Ala Gly Ala Gly Ser
            660                 665                 670
Gly Val Gly Val Pro Gly Val Gly Val Pro Gly Val Gly Val Pro Gly
        675                 680                 685
Lys Gly Val Pro Gly Val Gly Pro Gly Val Gly Pro Gly Val Gly Pro
690                 695                 700
Gly Val Gly Pro Gly Ala Gly Ala Gly Ser Gly Ala Gly Ala Gly Ser
705                 710                 715                 720
Gly Ala Gly Ala Gly Ser Gly Ala Gly Ala Gly Ser Gly Val Gly Val
            725                 730                 735
Pro Gly Val Gly Val Pro Gly Val Gly Val Pro Gly Lys Gly Val Pro
            740                 745                 750
Gly Val Gly Pro Gly Val Gly Pro Gly Val Gly Pro Gly Val Gly Pro
        755                 760                 765
Gly Ala Gly Ala Gly Ser Gly Ala Gly Ala Gly Ser
    770                 775                 780

<210> SEQ ID NO 20
<211> LENGTH: 3
<212> TYPE: PRT
<213> ORGANISM: unknown
<220> FEATURE:
<223> OTHER INFORMATION: artificial repeat sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 20

Gly Xaa Xaa
1

<210> SEQ ID NO 21
<211> LENGTH: 39
<212> TYPE: PRT
<213> ORGANISM: unknown
<220> FEATURE:
<223> OTHER INFORMATION: artificial repeat sequence

<400> SEQUENCE: 21

Gly Gly Gly Ala Gly Thr Thr Gly Gly Thr Gly Thr Ala Cys Cys Thr
1               5                   10                  15
Gly Gly Ala Gly Ala Ala Gly Gly Thr Gly Thr Thr Cys Cys Gly Gly
            20                  25                  30
Gly Gly Gly Thr Ala Gly Gly
        35

<210> SEQ ID NO 22
<211> LENGTH: 39
<212> TYPE: PRT
<213> ORGANISM: unknown
<220> FEATURE:
```

<223> OTHER INFORMATION: artificial glycine-rich peptide

<400> SEQUENCE: 22

Cys Cys Cys Thr Cys Ala Ala Cys Cys Ala Cys Ala Thr Gly Gly Ala
1               5                   10                  15

Cys Cys Thr Cys Thr Thr Cys Cys Ala Cys Ala Ala Gly Gly Cys Cys
                20                  25                  30

Cys Cys Cys Ala Thr Cys Cys
            35

<210> SEQ ID NO 23
<211> LENGTH: 39
<212> TYPE: PRT
<213> ORGANISM: unknown
<220> FEATURE:
<223> OTHER INFORMATION: metallothionin peptide segments

<400> SEQUENCE: 23

Gly Gly Gly Ala Gly Thr Thr Gly Gly Gly Thr Ala Cys Cys Thr
1               5                   10                  15

Gly Gly Ala Cys Gly Ala Gly Gly Thr Gly Thr Thr Cys Cys Gly Gly
                20                  25                  30

Gly Gly Gly Thr Ala Gly Gly
            35

<210> SEQ ID NO 24
<211> LENGTH: 39
<212> TYPE: PRT
<213> ORGANISM: unknown
<220> FEATURE:
<223> OTHER INFORMATION: artificial glycine-rich peptide repeat

<400> SEQUENCE: 24

Gly Gly Gly Ala Gly Thr Thr Gly Gly Gly Thr Ala Cys Cys Thr
1               5                   10                  15

Gly Gly Ala Cys Gly Ala Gly Gly Thr Gly Thr Thr Cys Cys Gly Gly
                20                  25                  30

Gly Gly Gly Thr Ala Gly Gly
            35

<210> SEQ ID NO 25
<211> LENGTH: 884
<212> TYPE: PRT
<213> ORGANISM: unknown
<220> FEATURE:
<223> OTHER INFORMATION: artificial glycine-rich peptide repeat sequence

<400> SEQUENCE: 25

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Val Val Pro
            35                  40                  45

Gly Val Gly Val Pro Gly Val Gly Val Pro Gly Val Gly Val Pro Gly
        50                  55                  60

Glu Gly Val Pro Gly Val Gly Val Pro Gly Val Gly Glu Pro Gly Val
65                  70                  75                  80

Gly Val Pro Gly Ala Gly Ala Gly Ser Gly Ala Gly Ala Gly Ser Gly
                85                  90                  95

-continued

```
Ala Gly Ala Gly Ser Gly Ala Gly Ala Gly Ser Gly Val Gly Val Pro
            100                 105                 110
Gly Val Gly Val Pro Gly Val Gly Val Pro Gly Val Gly Val Pro Gly
        115                 120                 125
Glu Gly Val Pro Gly Val Gly Val Pro Gly Val Gly Glu Pro Gly Val
        130                 135                 140
Gly Val Pro Gly Ala Gly Ala Gly Ser Gly Ala Gly Ala Gly Ser Gly
145                 150                 155                 160
Ala Gly Ala Gly Ser Gly Ala Gly Ala Gly Ser Gly Val Gly Val Pro
            165                 170                 175
Gly Val Gly Val Pro Gly Val Gly Val Pro Gly Val Gly Val Pro Gly
        180                 185                 190
Glu Gly Val Pro Gly Val Gly Val Pro Gly Val Gly Glu Pro Gly Val
        195                 200                 205
Gly Val Pro Gly Ala Gly Ala Gly Ser Gly Ala Gly Ala Gly Ser Gly
        210                 215                 220
Ala Gly Ala Gly Ser Gly Ala Gly Ala Gly Ser Gly Val Gly Val Pro
225                 230                 235                 240
Gly Val Gly Val Pro Gly Val Gly Val Pro Gly Val Gly Val Pro Gly
            245                 250                 255
Glu Gly Val Pro Gly Val Gly Val Pro Gly Val Gly Glu Pro Gly Val
        260                 265                 270
Gly Val Pro Gly Ala Gly Ala Gly Ser Gly Ala Gly Ala Gly Ser Gly
        275                 280                 285
Ala Gly Ala Gly Ser Gly Ala Gly Ala Gly Ser Gly Val Gly Val Pro
        290                 295                 300
Gly Val Gly Val Pro Gly Val Gly Val Pro Gly Val Gly Val Pro Gly
305                 310                 315                 320
Glu Gly Val Pro Gly Val Gly Val Pro Gly Val Gly Glu Pro Gly Val
            325                 330                 335
Gly Val Pro Gly Ala Gly Ala Gly Ser Gly Ala Gly Ala Gly Ser Gly
        340                 345                 350
Ala Gly Ala Gly Ser Gly Ala Gly Ala Gly Ser Gly Val Gly Val Pro
        355                 360                 365
Gly Val Gly Val Pro Gly Val Gly Val Pro Gly Val Gly Val Pro Gly
        370                 375                 380
Glu Gly Val Pro Gly Val Gly Val Pro Gly Val Gly Glu Pro Gly Val
385                 390                 395                 400
Gly Val Pro Gly Ala Gly Ala Gly Ser Gly Ala Gly Ala Gly Ser Gly
            405                 410                 415
Ala Gly Ala Gly Ser Gly Ala Gly Ala Gly Ser Gly Val Gly Val Pro
        420                 425                 430
Gly Val Gly Val Pro Gly Val Gly Val Pro Gly Val Gly Val Pro Gly
        435                 440                 445
Glu Gly Val Pro Gly Val Gly Val Pro Gly Val Gly Glu Pro Gly Val
        450                 455                 460
Gly Val Pro Gly Ala Gly Ala Gly Ser Gly Ala Gly Ala Gly Ser Gly
465                 470                 475                 480
Ala Gly Ala Gly Ser Gly Ala Gly Ala Gly Ser Gly Val Gly Val Pro
            485                 490                 495
Gly Val Gly Val Pro Gly Val Gly Val Pro Gly Val Gly Val Pro Gly
        500                 505                 510
Glu Gly Val Pro Gly Val Gly Val Pro Gly Val Gly Glu Pro Gly Val
```

```
                515                 520                 525
Gly Val Pro Gly Ala Gly Ala Gly Ser Gly Ala Gly Ala Gly Ser Gly
            530                 535                 540
Ala Gly Ala Gly Ser Gly Ala Gly Ala Gly Ser Gly Val Gly Val Pro
545                 550                 555                 560
Gly Val Gly Val Pro Gly Val Gly Val Pro Gly Val Gly Val Pro Gly
                565                 570                 575
Glu Gly Val Pro Gly Val Gly Val Pro Gly Val Gly Glu Pro Gly Val
            580                 585                 590
Gly Val Pro Gly Ala Gly Ala Gly Ser Gly Ala Gly Ala Gly Ser Gly
            595                 600                 605
Ala Gly Ala Gly Ser Gly Ala Gly Ala Gly Ser Gly Val Gly Val Pro
            610                 615                 620
Gly Val Gly Val Pro Gly Val Gly Val Pro Gly Val Gly Val Pro Gly
625                 630                 635                 640
Glu Gly Val Pro Gly Val Gly Val Pro Gly Val Gly Glu Pro Gly Val
                645                 650                 655
Gly Val Pro Gly Ala Gly Ala Gly Ser Gly Ala Gly Ala Gly Ser Gly
            660                 665                 670
Ala Gly Ala Gly Ser Gly Ala Gly Ala Gly Ser Gly Val Gly Val Pro
            675                 680                 685
Gly Val Gly Val Pro Gly Val Gly Val Pro Gly Val Gly Val Pro Gly
            690                 695                 700
Glu Gly Val Pro Gly Val Gly Val Pro Gly Val Gly Glu Pro Gly Val
705                 710                 715                 720
Gly Val Pro Gly Ala Gly Ala Gly Ser Gly Ala Gly Ala Gly Ser Gly
                725                 730                 735
Ala Gly Ala Gly Ser Gly Ala Gly Ala Gly Ser Gly Val Gly Val Pro
            740                 745                 750
Gly Val Gly Val Pro Gly Val Gly Val Pro Gly Val Gly Val Pro Gly
            755                 760                 765
Glu Gly Val Pro Gly Val Gly Val Pro Gly Val Gly Glu Pro Gly Val
            770                 775                 780
Gly Val Pro Gly Ala Gly Ala Gly Ser Gly Ala Gly Ala Gly Ser Gly
785                 790                 795                 800
Ala Gly Ala Gly Ser Gly Ala Gly Ala Gly Ser Gly Val Gly Val Pro
                805                 810                 815
Gly Val Gly Val Pro Gly Val Gly Val Pro Gly Val Gly Val Pro Gly
            820                 825                 830
Glu Gly Val Pro Gly Val Gly Val Pro Gly Val Gly Glu Pro Gly Val
            835                 840                 845
Gly Val Pro Gly Ala Gly Ala Gly Ser Gly Ala Gly Ala Gly Ser Gly
            850                 855                 860
Ala Gly Ala Met Asp Pro Gly Arg Tyr Gln Asp Leu Arg Ser His His
865                 870                 875                 880
His His His His

<210> SEQ ID NO 26
<211> LENGTH: 246
<212> TYPE: PRT
<213> ORGANISM: unknown
<220> FEATURE:
<223> OTHER INFORMATION: silk and elastin peptide repeat sequence

<400> SEQUENCE: 26
```

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
        35                  40                  45

Val Pro Gly Val Gly Val Pro Gly Val Gly Val Pro Gly Val Gly Val
    50                  55                  60

Pro Gly Arg Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
                85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
        115                 120                 125

Pro Gly Arg Gly Val Pro Gly Val Gly Val Pro Gly Val Gly Val Pro
    130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Arg Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
    210                 215                 220

Ser Gly Ala Gly Ala Met Asp Pro Gly Arg Tyr Gln Asp Leu Arg Ser
225                 230                 235                 240

His His His His His His
                245

<210> SEQ ID NO 27
<211> LENGTH: 244
<212> TYPE: PRT
<213> ORGANISM: unknown
<220> FEATURE:
<223> OTHER INFORMATION: silk and elastin peptide repeat sequence

<400> SEQUENCE: 27

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110
```

Gly Val Gly Val Pro Gly Val Gly Val Pro Gly Val Gly Val Pro Gly
            115                 120                 125

Lys Gly Val Pro Gly Val Gly Val Pro Gly Val Gly Val Pro Gly Val
            130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
            165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
            195                 200                 205

Gly Val Pro Gly Ala Gly Ala Gly Ser Gly Ala Gly Ala Gly Ser Gly
            210                 215                 220

Ala Gly Ala Met Asp Pro Gly Arg Tyr Gln Asp Leu Arg Ser His His
225                 230                 235                 240

His His His His

<210> SEQ ID NO 28
<211> LENGTH: 246
<212> TYPE: PRT
<213> ORGANISM: unknown
<220> FEATURE:
<223> OTHER INFORMATION: silk and elastin peptide repeat sequence

<400> SEQUENCE: 28

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ala Gly Ser Gly Ala Gly Ala Gly Ser Gly Val Gly
            35                  40                  45

Val Pro Gly Val Gly Val Pro Gly Val Gly Val Pro Gly Val Gly Val
            50                  55                  60

Pro Gly Glu Gly Val Pro Gly Val Gly Val Pro Gly Val Gly Val Pro
65                  70                  75                  80

Gly Val Gly Val Pro Gly Ala Gly Ala Gly Ser Gly Ala Gly Ala Gly
            85                  90                  95

Ser Gly Ala Gly Ala Gly Ser Gly Ala Gly Ala Gly Ser Gly Val Gly
            100                 105                 110

Val Pro Gly Val Gly Val Pro Gly Val Gly Val Pro Gly Val Gly Val
            115                 120                 125

Pro Gly Glu Gly Val Pro Gly Val Gly Val Pro Gly Val Gly Val Pro
            130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
            165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
            195                 200                 205

Gly Val Gly Val Pro Gly Ala Gly Ala Gly Ser Gly Ala Gly Ala Gly
            210                 215                 220

```
Ser Gly Ala Gly Ala Met Asp Pro Gly Arg Tyr Gln Asp Leu Arg Ser
225                 230                 235                 240

His His His His His His
                245

<210> SEQ ID NO 29
<211> LENGTH: 1063
<212> TYPE: PRT
<213> ORGANISM: unknown
<220> FEATURE:
<223> OTHER INFORMATION: silk and elastin peptide repeat sequence

<400> SEQUENCE: 29

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala His Gly Pro Ala Gly Pro Lys Gly Ala His Gly Pro Ala
            35                  40                  45

Gly Pro Lys Gly Ala Gln Gly Pro Ala Gly Pro Gly Gly Ala Gln Gly
        50                  55                  60

Pro Ala Gly Pro Gly Gly Ala Gln Gly Pro Ala Gly Pro Gly Gly Ala
65                  70                  75                  80

Gln Gly Pro Ala Gly Pro Gly Gly Ala Gln Gly Pro Ala Gly Pro Gly
                85                  90                  95

Gly Ala Gln Gly Pro Ala Gly Pro Gly Gly Ala Gln Gly Pro Ala Gly
            100                 105                 110

Pro Gly Gly Ala Gln Gly Pro Ala Gly Pro Gly Gly Ala Gln Gly Pro
        115                 120                 125

Ala Gly Pro Gly Gly Ala Gln Gly Pro Ala Gly Pro Gly Gly Ala Gln
    130                 135                 140

Gly Pro Ala Gly Pro Gly Gly Ala Gln Gly Pro Ala Gly Pro Gly Gly
145                 150                 155                 160

Ala Gln Gly Pro Ala Gly Pro Gly Gly Ala Gln Gly Pro Ala Gly Pro
                165                 170                 175

Gly Gly Ala Gln Gly Pro Ala Gly Pro Gly Gly Ala Gln Gly Pro Ala
            180                 185                 190

Gly Pro Gly Gly Ala Gln Gly Pro Ala Gly Pro Gly Gly Ala Gln Gly
        195                 200                 205

Pro Ala Gly Pro Gly Gly Ala Gln Gly Pro Ala Gly Pro Gly Gly Ala
    210                 215                 220

Gln Gly Pro Ala Gly Pro Gly Gly Ala Gln Gly Pro Ala Gly Pro Gly
225                 230                 235                 240

Gly Ala Gln Gly Pro Ala Gly Pro Gly Gly Ala Gln Gly Pro Ala Gly
                245                 250                 255

Pro Gly Gly Ala Gln Gly Pro Ala Gly Pro Gly Gly Ala His Gly Pro
            260                 265                 270

Ala Gly Pro Lys Gly Ala His Gly Pro Ala Gly Pro Lys Gly Ala His
        275                 280                 285

Gly Pro Ala Gly Pro Lys Gly Ala His Gly Pro Ala Gly Pro Lys Gly
    290                 295                 300

Ala Gln Gly Pro Ala Gly Pro Gly Gly Ala Gln Gly Pro Ala Gly Pro
305                 310                 315                 320

Gly Gly Ala Gln Gly Pro Ala Gly Pro Gly Gly Ala Gln Gly Pro Ala
                325                 330                 335
```

-continued

Gly Pro Gly Gly Ala Gln Gly Pro Ala Gly Pro Gly Gly Ala Gln Gly
            340                 345                 350

Pro Ala Gly Pro Gly Gly Ala Gln Gly Pro Ala Gly Pro Gly Gly Ala
            355                 360                 365

Gln Gly Pro Ala Gly Pro Gly Gly Ala Gln Gly Pro Ala Gly Pro Gly
            370                 375                 380

Gly Ala Gln Gly Pro Ala Gly Pro Gly Gly Ala Gln Gly Pro Ala Gly
385                 390                 395                 400

Pro Gly Gly Ala Gln Gly Pro Ala Gly Pro Gly Gly Ala Gln Gly Pro
            405                 410                 415

Ala Gly Pro Gly Gly Ala Gln Gly Pro Ala Gly Pro Gly Gly Ala Gln
            420                 425                 430

Gly Pro Ala Gly Pro Gly Gly Ala Gln Gly Pro Ala Gly Pro Gly Gly
            435                 440                 445

Ala Gln Gly Pro Ala Gly Pro Gly Gly Ala Gln Gly Pro Ala Gly Pro
            450                 455                 460

Gly Gly Ala Gln Gly Pro Ala Gly Pro Gly Gly Ala Gln Gly Pro Ala
465                 470                 475                 480

Gly Pro Gly Gly Ala Gln Gly Pro Ala Gly Pro Gly Gly Ala Gln Gly
            485                 490                 495

Pro Ala Gly Pro Gly Gly Ala Gln Gly Pro Ala Gly Pro Gly Gly Ala
            500                 505                 510

Gln Gly Pro Ala Gly Pro Gly Gly Ala His Gly Pro Ala Gly Pro Lys
            515                 520                 525

Gly Ala His Gly Pro Ala Gly Pro Lys Gly Ala His Gly Pro Ala Gly
            530                 535                 540

Pro Lys Gly Ala His Gly Pro Ala Gly Pro Lys Gly Ala Gln Gly Pro
545                 550                 555                 560

Ala Gly Pro Gly Gly Ala Gln Gly Pro Ala Gly Pro Gly Gly Ala Gln
            565                 570                 575

Gly Pro Ala Gly Pro Gly Gly Ala Gln Gly Pro Ala Gly Pro Gly Gly
            580                 585                 590

Ala Gln Gly Pro Ala Gly Pro Gly Gly Ala Gln Gly Pro Ala Gly Pro
            595                 600                 605

Gly Gly Ala Gln Gly Pro Ala Gly Pro Gly Gly Ala Gln Gly Pro Ala
            610                 615                 620

Gly Pro Gly Gly Ala Gln Gly Pro Ala Gly Pro Gly Gly Ala Gln Gly
625                 630                 635                 640

Pro Ala Gly Pro Gly Gly Ala Gln Gly Pro Ala Gly Pro Gly Gly Ala
            645                 650                 655

Gln Gly Pro Ala Gly Pro Gly Gly Ala Gln Gly Pro Ala Gly Pro Gly
            660                 665                 670

Gly Ala Gln Gly Pro Ala Gly Pro Gly Gly Ala Gln Gly Pro Ala Gly
            675                 680                 685

Pro Gly Gly Ala Gln Gly Pro Ala Gly Pro Gly Gly Ala Gln Gly Pro
            690                 695                 700

Ala Gly Pro Gly Gly Ala Gln Gly Pro Ala Gly Pro Gly Gly Ala Gln
705                 710                 715                 720

Gly Pro Ala Gly Pro Gly Gly Ala Gln Gly Pro Ala Gly Pro Gly Gly
            725                 730                 735

Ala Gln Gly Pro Ala Gly Pro Gly Gly Ala Gln Gly Pro Ala Gly Pro
            740                 745                 750

Gly Gly Ala Gln Gly Pro Ala Gly Pro Gly Gly Ala Gln Gly Pro Ala

-continued

```
              755                 760                 765
Gly Pro Gly Gly Ala His Gly Pro Ala Gly Pro Lys Gly Ala His Gly
            770                 775                 780
Pro Ala Gly Pro Lys Gly Ala His Gly Pro Ala Gly Pro Lys Gly Ala
785                 790                 795                 800
His Gly Pro Ala Gly Pro Lys Gly Ala Gln Gly Pro Ala Gly Pro Gly
                805                 810                 815
Gly Ala Gln Gly Pro Ala Gly Pro Gly Gly Ala Gln Gly Pro Ala Gly
            820                 825                 830
Pro Gly Gly Ala Gln Gly Pro Ala Gly Pro Gly Gly Ala Gln Gly Pro
            835                 840                 845
Ala Gly Pro Gly Gly Ala Gln Gly Pro Ala Gly Pro Gly Gly Ala Gln
            850                 855                 860
Gly Pro Ala Gly Pro Gly Gly Ala Gln Gly Pro Ala Gly Pro Gly Gly
865                 870                 875                 880
Ala Gln Gly Pro Ala Gly Pro Gly Gly Ala Gln Gly Pro Ala Gly Pro
                885                 890                 895
Gly Gly Ala Gln Gly Pro Ala Gly Pro Gly Gly Ala Gln Gly Pro Ala
            900                 905                 910
Gly Pro Gly Gly Ala Gln Gly Pro Ala Gly Pro Gly Gly Ala Gln Gly
            915                 920                 925
Pro Ala Gly Pro Gly Gly Ala Gln Gly Pro Ala Gly Pro Gly Gly Ala
            930                 935                 940
Gln Gly Pro Ala Gly Pro Gly Gly Ala Gln Gly Pro Ala Gly Pro Gly
945                 950                 955                 960
Gly Ala Gln Gly Pro Ala Gly Pro Gly Gly Ala Gln Gly Pro Ala Gly
                965                 970                 975
Pro Gly Gly Ala Gln Gly Pro Ala Gly Pro Gly Gly Ala Gln Gly Pro
            980                 985                 990
Ala Gly Pro Gly Gly Ala Gln Gly  Pro Ala Gly Pro Gly  Gly Ala Gln
            995                 1000                 1005
Gly Pro  Ala Gly Pro Gly Gly  Ala Gln Gly Pro Ala  Gly Pro Gly
          1010                1015                1020
Gly Ala  His Gly Pro Ala Gly  Pro Lys Gly Ala His  Gly Pro Ala
          1025                1030                1035
Gly Pro  Lys Met Asp Pro Gly  Arg Tyr Gln Leu Ser  Ala Gly Arg
          1040                1045                1050
Tyr His  Tyr Gln Leu Val Trp  Cys Gln Lys
          1055                1060

<210> SEQ ID NO 30
<211> LENGTH: 1038
<212> TYPE: PRT
<213> ORGANISM: unknown
<220> FEATURE:
<223> OTHER INFORMATION: artificial repeat sequence

<400> SEQUENCE: 30

Met Asp Pro Val Val Leu Gln Arg Arg Asp Trp Glu Asn Pro Gly Val
1               5                  10                  15

Thr Gln Leu Asn Arg Leu Ala Ala His Pro Pro Phe Ala Ser Asp Pro
                20                  25                  30

Met Gly Val Gly Val Pro Gly Val Gly Val Pro Gly Val Gly Val Pro
            35                  40                  45

Gly Val Gly Val Pro Gly Lys Gly Val Pro Gly Val Gly Val Pro Gly
```

-continued

```
                50                  55                  60
Val Gly Val Pro Gly Val Gly Val Pro Gly Ala Gly Ala Gly Ser Gly
 65                  70                  75                  80

Ala Gly Ala Gly Ser Gly Ala Gly Ala Gly Ser Gly Ala Gly Ala Gly
                 85                  90                  95

Ser Gly Ala Gly Ala Gly Ser Gly Ala Gly Ala Gly Ser Gly Val Gly
                100                 105                 110

Val Pro Gly Val Gly Val Pro Gly Val Gly Val Pro Gly Val Gly Val
                115                 120                 125

Pro Gly Lys Gly Val Pro Gly Val Gly Val Pro Gly Val Gly Val Pro
                130                 135                 140

Gly Val Gly Val Pro Gly Ala Gly Ala Gly Ser Gly Ala Gly Ala Gly
145                 150                 155                 160

Ser Gly Ala Gly Ala Gly Ser Gly Ala Gly Ala Gly Ser Gly Ala Gly
                165                 170                 175

Ala Gly Ser Gly Ala Gly Ala Gly Ser Gly Val Gly Val Pro Gly Val
                180                 185                 190

Gly Val Pro Gly Val Gly Val Pro Gly Val Gly Val Pro Gly Lys Gly
                195                 200                 205

Val Pro Gly Val Gly Val Pro Gly Val Gly Val Pro Gly Val Gly Val
                210                 215                 220

Pro Gly Ala Gly Ala Gly Ser Gly Ala Gly Ala Gly Ser Gly Ala Gly
225                 230                 235                 240

Ala Gly Ser Gly Ala Gly Ala Gly Ser Gly Ala Gly Ala Gly Ser Gly
                245                 250                 255

Ala Gly Ala Gly Ser Gly Val Gly Val Pro Gly Val Gly Val Pro Gly
                260                 265                 270

Val Gly Val Pro Gly Val Gly Val Pro Gly Lys Gly Val Pro Gly Val
                275                 280                 285

Gly Val Pro Gly Val Gly Val Pro Gly Val Gly Val Pro Gly Ala Gly
                290                 295                 300

Ala Gly Ser Gly Ala Gly Ala Gly Ser Gly Ala Gly Ala Gly Ser Gly
305                 310                 315                 320

Ala Gly Ala Gly Ser Gly Ala Gly Ala Gly Ser Gly Ala Gly Ala Gly
                325                 330                 335

Ser Gly Val Gly Val Pro Gly Val Gly Val Pro Gly Val Gly Val Pro
                340                 345                 350

Gly Val Gly Val Pro Gly Lys Gly Val Pro Gly Val Gly Val Pro Gly
                355                 360                 365

Val Gly Val Pro Gly Val Gly Val Pro Gly Ala Gly Ala Gly Ser Gly
                370                 375                 380

Ala Gly Ala Gly Ser Gly Ala Gly Ala Gly Ser Gly Ala Gly Ala Gly
385                 390                 395                 400

Ser Gly Ala Gly Ala Gly Ser Gly Ala Gly Ala Gly Ser Gly Val Gly
                405                 410                 415

Val Pro Gly Val Gly Val Pro Gly Val Gly Val Pro Gly Val Gly Val
                420                 425                 430

Pro Gly Lys Gly Val Pro Gly Val Gly Val Pro Gly Val Gly Val Pro
                435                 440                 445

Gly Val Gly Val Pro Gly Ala Gly Ala Gly Ser Gly Ala Gly Ala Gly
                450                 455                 460

Ser Gly Ala Gly Ala Gly Ser Gly Ala Gly Ala Gly Ser Gly Ala Gly
465                 470                 475                 480
```

-continued

```
Ala Gly Ser Gly Ala Gly Ala Gly Ser Gly Val Gly Val Pro Gly Val
            485                 490                 495
Gly Val Pro Gly Val Gly Val Pro Gly Val Gly Val Pro Gly Lys Gly
        500                 505                 510
Val Pro Gly Val Gly Val Pro Gly Val Gly Val Pro Gly Val Gly Val
            515                 520                 525
Pro Gly Ala Gly Ala Gly Ser Gly Ala Gly Ala Gly Ser Gly Ala Gly
        530                 535                 540
Ala Gly Ser Gly Ala Gly Ala Gly Ser Gly Ala Gly Ala Gly Ser Gly
545                 550                 555                 560
Ala Gly Ala Gly Ser Gly Val Gly Val Pro Gly Val Gly Val Pro Gly
            565                 570                 575
Val Gly Val Pro Gly Val Gly Val Pro Gly Lys Gly Val Pro Gly Val
        580                 585                 590
Gly Val Pro Gly Val Gly Val Pro Gly Val Gly Val Pro Gly Ala Gly
    595                 600                 605
Ala Gly Ser Gly Ala Gly Ala Gly Ser Gly Ala Gly Ala Gly Ser Gly
        610                 615                 620
Ala Gly Ala Gly Ser Gly Ala Gly Ala Gly Ser Gly Ala Gly Ala Gly
625                 630                 635                 640
Ser Gly Val Gly Val Pro Gly Val Gly Val Pro Gly Val Gly Val Pro
            645                 650                 655
Gly Val Gly Val Pro Gly Lys Gly Val Pro Gly Val Gly Val Pro Gly
        660                 665                 670
Val Gly Val Pro Gly Val Gly Val Pro Gly Ala Gly Ala Gly Ser Gly
            675                 680                 685
Ala Gly Ala Gly Ser Gly Ala Gly Ala Gly Ser Gly Ala Gly Ala Gly
        690                 695                 700
Ser Gly Ala Gly Ala Gly Ser Gly Ala Gly Ala Gly Ser Gly Val Gly
705                 710                 715                 720
Val Pro Gly Val Gly Val Pro Gly Val Gly Val Pro Gly Val Gly Val
            725                 730                 735
Pro Gly Lys Gly Val Pro Gly Val Gly Val Pro Gly Val Gly Val Pro
        740                 745                 750
Gly Val Gly Val Pro Gly Ala Gly Ala Gly Ser Gly Ala Gly Ala Gly
    755                 760                 765
Ser Gly Ala Gly Ala Gly Ser Gly Ala Gly Ala Gly Ser Gly Ala Gly
        770                 775                 780
Ala Gly Ser Gly Ala Gly Ala Gly Ser Gly Val Gly Val Pro Gly Val
785                 790                 795                 800
Gly Val Pro Gly Val Gly Val Pro Gly Val Gly Val Pro Gly Lys Gly
            805                 810                 815
Val Pro Gly Val Gly Val Pro Gly Val Gly Val Pro Gly Val Gly Val
        820                 825                 830
Pro Gly Ala Gly Ala Gly Ser Gly Ala Gly Ala Gly Ser Gly Ala Gly
    835                 840                 845
Ala Gly Ser Gly Ala Gly Ala Gly Ser Gly Ala Gly Ala Gly Ser Gly
        850                 855                 860
Ala Gly Ala Gly Ser Gly Val Gly Val Pro Gly Val Gly Val Pro Gly
865                 870                 875                 880
Val Gly Val Pro Gly Val Gly Val Pro Gly Lys Gly Val Pro Gly Val
            885                 890                 895
```

```
Gly Val Pro Gly Val Gly Val Pro Gly Val Gly Val Pro Gly Ala Gly
                900                 905                 910

Ala Gly Ser Gly Ala Gly Ala Gly Ser Gly Ala Gly Ala Gly Ser Gly
            915                 920                 925

Ala Gly Ala Gly Ser Gly Ala Gly Ala Gly Ser Gly Ala Gly Ala Gly
        930                 935                 940

Ser Gly Val Gly Val Pro Gly Val Gly Val Pro Gly Val Gly Val Pro
945                 950                 955                 960

Gly Val Gly Val Pro Gly Lys Gly Val Pro Gly Val Gly Val Pro Gly
                965                 970                 975

Val Gly Val Pro Gly Val Gly Val Pro Gly Ala Gly Ala Gly Ser Gly
            980                 985                 990

Ala Gly Ala Gly Ser Gly Ala Gly Ala Gly Ser Gly Ala Gly Ala Gly
        995                1000                1005

Ser Gly Ala Gly Ala Gly Ser Gly Ala Gly Ala Gly Ser Met Asp
       1010                1015                1020

Pro Gly Arg Tyr Gln Asp Leu Arg Ser His His His His His His
       1025                1030                1035

<210> SEQ ID NO 31
<211> LENGTH: 965
<212> TYPE: PRT
<213> ORGANISM: unknown
<220> FEATURE:
<223> OTHER INFORMATION: silk and elastin peptides

<400> SEQUENCE: 31

Met Asp Pro Val Val Leu Gln Arg Arg Asp Trp Glu Asn Pro Gly Val
1               5                  10                  15

Thr Gln Leu Asn Arg Leu Ala Ala His Pro Pro Phe Ala Ser Asp Pro
            20                  25                  30

Met Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Ala Gly Ala Gly Ser Gly
65                  70                  75                  80

Ala Gly Ala Gly Ser Gly Ala Gly Ala Gly Ser Gly Ala Gly Ala Gly
                85                  90                  95

Ser Gly Ala Gly Ala Gly Ser Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Ala Gly Ala Gly Ser Gly Ala Gly Ala Gly Ser Gly Ala Gly Ala Gly
145                 150                 155                 160

Ser Gly Ala Gly Ala Gly Ser Gly Ala Gly Ala Gly Ser Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Ala Gly Ala Gly Ser Gly Ala Gly Ala Gly
    210                 215                 220
```

-continued

```
Ser Gly Ala Gly Ala Gly Ser Gly Ala Gly Ala Gly Ser Gly Ala Gly
225                 230                 235                 240
Ala Gly Ser Gly Val Gly Val Pro Gly Val Gly Val Pro Gly Val Gly
                245                 250                 255
Val Pro Gly Val Gly Val Pro Gly Val Gly Val Pro Gly Val Gly Val
                260                 265                 270
Pro Gly Val Gly Val Pro Gly Val Gly Val Pro Gly Ala Gly Ala Gly
                275                 280                 285
Ser Gly Ala Gly Ala Gly Ser Gly Ala Gly Ala Gly Ser Gly Ala Gly
                290                 295                 300
Ala Gly Ser Gly Ala Gly Ala Gly Ser Gly Val Gly Val Pro Gly Val
305                 310                 315                 320
Gly Val Pro Gly Val Gly Val Pro Gly Val Gly Val Pro Gly Val Gly
                325                 330                 335
Val Pro Gly Val Gly Val Pro Gly Val Gly Val Pro Gly Val Gly Val
                340                 345                 350
Pro Gly Ala Gly Ala Gly Ser Gly Ala Gly Ala Gly Ser Gly Ala Gly
                355                 360                 365
Ala Gly Ser Gly Ala Gly Ala Gly Ser Gly Ala Gly Ala Gly Ser Gly
                370                 375                 380
Val Gly Val Pro Gly Val Gly Val Pro Gly Val Gly Val Pro Gly Val
385                 390                 395                 400
Gly Val Pro Gly Val Gly Val Pro Gly Val Gly Val Pro Gly Val Gly
                405                 410                 415
Val Pro Gly Val Gly Val Pro Gly Ala Gly Ala Gly Ser Gly Ala Gly
                420                 425                 430
Ala Gly Ser Gly Ala Gly Ser Gly Ala Gly Ala Gly Ser Gly
                435                 440                 445
Ala Gly Ala Gly Ser Gly Val Gly Val Pro Gly Val Gly Val Pro Gly
                450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Ala Gly
                485                 490                 495
Ala Gly Ser Gly Ala Gly Ala Gly Ser Gly Ala Gly Ala Gly Ser Gly
                500                 505                 510
Ala Gly Ala Gly Ser Gly Ala Gly Ala Gly Ser Gly Val Gly Val Pro
                515                 520                 525
Gly Val Gly Val Pro Gly Val Gly Val Pro Gly Val Gly Val Pro Gly
                530                 535                 540
Val Gly Val Pro Gly Val Gly Val Pro Gly Val Gly Val Pro Gly Val
545                 550                 555                 560
Gly Val Pro Gly Ala Gly Ala Gly Ser Gly Ala Gly Ala Gly Ser Gly
                565                 570                 575
Ala Gly Ala Gly Ser Gly Ala Gly Ala Gly Ser Gly Ala Gly Ala Gly
                580                 585                 590
Ser Gly Val Gly Val Pro Gly Val Gly Val Pro Gly Val Gly Val Pro
                595                 600                 605
Gly Val Gly Val Pro Gly Val Gly Val Pro Gly Val Gly Val Pro Gly
                610                 615                 620
Val Gly Val Pro Gly Val Gly Val Pro Gly Ala Gly Ala Gly Ser Gly
625                 630                 635                 640
Ala Gly Ala Gly Ser Gly Ala Gly Ala Gly Ser Gly Ala Gly Ala Gly
```

-continued

```
                    645                 650                 655
Ser Gly Ala Gly Ala Gly Ser Gly Val Gly Val Pro Gly Val Gly Val
            660                 665                 670

Pro Gly Val Gly Val Pro Gly Val Gly Val Pro Gly Val Gly Val Pro
        675                 680                 685

Gly Val Gly Val Pro Gly Val Gly Val Pro Gly Val Gly Val Pro Gly
    690                 695                 700

Ala Gly Ala Gly Ser Gly Ala Gly Ala Gly Ser Gly Ala Gly Ala Gly
705                 710                 715                 720

Ser Gly Ala Gly Ala Gly Ser Gly Ala Gly Ser Gly Val Gly
            725                 730                 735

Val Pro Gly Val Gly Val Pro Gly Val Gly Val Pro Gly Val Gly Val
        740                 745                 750

Pro Gly Val Gly Val Pro Gly Val Gly Val Pro Gly Val Gly Val Pro
    755                 760                 765

Gly Val Gly Val Pro Gly Ala Gly Ala Gly Ser Gly Ala Gly Ala Gly
770                 775                 780

Ser Gly Ala Gly Ala Gly Ser Gly Ala Gly Ala Gly Ser Gly Ala Gly
785                 790                 795                 800

Ala Gly Ser Gly Val Gly Val Pro Gly Val Gly Val Pro Gly Val Gly
            805                 810                 815

Val Pro Gly Val Gly Val Pro Gly Val Gly Val Pro Gly Val Gly Val
        820                 825                 830

Pro Gly Val Gly Val Pro Gly Val Gly Val Pro Gly Ala Gly Ala Gly
    835                 840                 845

Ser Gly Ala Gly Ala Gly Ser Gly Ala Gly Ala Gly Ser Gly Ala Gly
850                 855                 860

Ala Gly Ser Gly Ala Gly Ala Gly Ser Gly Val Gly Val Pro Gly Val
865                 870                 875                 880

Gly Val Pro Gly Val Gly Val Pro Gly Val Gly Val Pro Gly Val Gly
            885                 890                 895

Val Pro Gly Val Gly Val Pro Gly Val Gly Val Pro Gly Val Gly Val
        900                 905                 910

Pro Gly Ala Gly Ala Gly Ser Gly Ala Gly Ala Gly Ser Gly Ala Gly
    915                 920                 925

Ala Gly Ser Gly Ala Gly Ala Gly Ser Gly Ala Gly Ala Gly Ser Met
930                 935                 940

Asp Pro Gly Arg Tyr Gln Leu Ser Ala Gly Arg Tyr His Tyr Gln Leu
945                 950                 955                 960

Val Trp Cys Gln Lys
            965
```

<210> SEQ ID NO 32
<211> LENGTH: 1027
<212> TYPE: PRT
<213> ORGANISM: unknown
<220> FEATURE:
<223> OTHER INFORMATION: silk and elastin and cecropin A melletin peptide repeat sequences

<400> SEQUENCE: 32

```
Met Asp Pro His Met Arg Ser Leu Val Pro Arg Gly Ser Gly Gly Gly
1               5                   10                  15

Gly Gly Gly Lys Trp Lys Leu Phe Lys Lys Ile Gly Ala Val Leu Lys
            20                  25                  30
```

```
Val Leu Gly Gly Gly Gly Gly Lys Trp Lys Leu Phe Lys Lys Ile
         35                  40                  45
Gly Ala Val Leu Lys Val Leu Gly Gly Gly Gly Gly Lys Trp Lys
         50                  55                  60
Leu Phe Lys Lys Ile Gly Ala Val Leu Lys Val Leu Gly Gly Gly
 65                  70                  75                  80
Gly Gly Lys Trp Lys Leu Phe Lys Lys Ile Gly Ala Val Leu Lys Val
             85                  90                  95
Leu Gly Gly Gly Gly Gly Lys Trp Lys Leu Phe Lys Lys Ile Gly
            100                 105                 110
Ala Val Leu Lys Val Leu Gly Gly Gly Gly Gly Lys Trp Lys Leu
            115                 120                 125
Phe Lys Lys Ile Gly Ala Val Leu Lys Val Leu Lys Ile Cys Ile Trp
130                 135                 140
Asp Pro Val Val Leu Gln Arg Arg Asp Trp Glu Asn Pro Gly Val Thr
145                 150                 155                 160
Gln Leu Asn Arg Leu Ala Ala His Pro Pro Phe Ala Ser Asp Pro Met
            165                 170                 175
Gly Ala Gly Ser Gly Ala Gly Ala Gly Ser Gly Val Gly Val Pro Gly
            180                 185                 190
Val Gly Val Pro Gly Val Gly Val Pro Gly Val Gly Val Pro Gly Lys
            195                 200                 205
Gly Val Pro Gly Val Gly Val Pro Gly Val Gly Val Pro Gly Val Gly
            210                 215                 220
Val Pro Gly Ala Gly Ala Gly Ser Gly Ala Gly Ala Gly Ser Gly Ala
225                 230                 235                 240
Gly Ala Gly Ser Gly Ala Gly Ala Gly Ser Gly Val Gly Val Pro Gly
            245                 250                 255
Val Gly Val Pro Gly Val Gly Val Pro Gly Val Gly Val Pro Gly Lys
            260                 265                 270
Gly Val Pro Gly Val Gly Val Pro Gly Val Gly Val Pro Gly Val Gly
            275                 280                 285
Val Pro Gly Ala Gly Ala Gly Ser Gly Ala Gly Ala Gly Ser Gly Ala
290                 295                 300
Gly Ala Gly Ser Gly Ala Gly Ala Gly Ser Gly Val Gly Val Pro Gly
305                 310                 315                 320
Val Gly Val Pro Gly Val Gly Val Pro Gly Val Gly Val Pro Gly Lys
            325                 330                 335
Gly Val Pro Gly Val Gly Val Pro Gly Val Gly Val Pro Gly Val Gly
            340                 345                 350
Val Pro Gly Ala Gly Ala Gly Ser Gly Ala Gly Ala Gly Ser Gly Ala
            355                 360                 365
Gly Ala Gly Ser Gly Ala Gly Ala Gly Ser Gly Val Gly Val Pro Gly
370                 375                 380
Val Gly Val Pro Gly Val Gly Val Pro Gly Val Gly Val Pro Gly Lys
385                 390                 395                 400
Gly Val Pro Gly Val Gly Val Pro Gly Val Gly Val Pro Gly Val Gly
            405                 410                 415
Val Pro Gly Ala Gly Ala Gly Ser Gly Ala Gly Ala Gly Ser Gly Ala
            420                 425                 430
Gly Ala Gly Ser Gly Ala Gly Ala Gly Ser Gly Val Gly Val Pro Gly
            435                 440                 445
Val Gly Val Pro Gly Val Gly Val Pro Gly Val Gly Val Pro Gly Lys
```

-continued

```
            450                 455                 460
Gly Val Pro Gly Val Gly Val Pro Gly Val Gly Val Pro Gly Val Gly
465                 470                 475                 480
Val Pro Gly Ala Gly Ala Gly Ser Gly Ala Gly Ala Gly Ser Gly Ala
                485                 490                 495
Gly Ala Gly Ser Gly Ala Gly Ala Gly Ser Gly Val Gly Val Pro Gly
            500                 505                 510
Val Gly Val Pro Gly Val Gly Val Pro Gly Val Gly Val Pro Gly Lys
        515                 520                 525
Gly Val Pro Gly Val Gly Val Pro Gly Val Gly Val Pro Gly Val Gly
    530                 535                 540
Val Pro Gly Ala Gly Ala Gly Ser Gly Ala Gly Ala Gly Ser Gly Ala
545                 550                 555                 560
Gly Ala Gly Ser Gly Ala Gly Ala Gly Ser Gly Val Gly Val Pro Gly
                565                 570                 575
Val Gly Val Pro Gly Val Gly Val Pro Gly Val Gly Val Pro Gly Lys
            580                 585                 590
Gly Val Pro Gly Val Gly Val Pro Gly Val Gly Val Pro Gly Val Gly
        595                 600                 605
Val Pro Gly Ala Gly Ala Gly Ser Gly Ala Gly Ala Gly Ser Gly Ala
    610                 615                 620
Gly Ala Gly Ser Gly Ala Gly Ala Gly Ser Gly Val Gly Val Pro Gly
625                 630                 635                 640
Val Gly Val Pro Gly Val Gly Val Pro Gly Val Gly Val Pro Gly Lys
                645                 650                 655
Gly Val Pro Gly Val Gly Val Pro Gly Val Gly Val Pro Gly Val Gly
            660                 665                 670
Val Pro Gly Ala Gly Ala Gly Ser Gly Ala Gly Ala Gly Ser Gly Ala
        675                 680                 685
Gly Ala Gly Ser Gly Ala Gly Ala Gly Ser Gly Val Gly Val Pro Gly
    690                 695                 700
Val Gly Val Pro Gly Val Gly Val Pro Gly Val Gly Val Pro Gly Lys
705                 710                 715                 720
Gly Val Pro Gly Val Gly Val Pro Gly Val Gly Val Pro Gly Val Gly
                725                 730                 735
Val Pro Gly Ala Gly Ala Gly Ser Gly Ala Gly Ala Gly Ser Gly Ala
            740                 745                 750
Gly Ala Gly Ser Gly Ala Gly Ala Gly Ser Gly Val Gly Val Pro Gly
        755                 760                 765
Val Gly Val Pro Gly Val Gly Val Pro Gly Val Gly Val Pro Gly Lys
    770                 775                 780
Gly Val Pro Gly Val Gly Val Pro Gly Val Gly Val Pro Gly Val Gly
785                 790                 795                 800
Val Pro Gly Ala Gly Ala Gly Ser Gly Ala Gly Ala Gly Ser Gly Ala
                805                 810                 815
Gly Ala Gly Ser Gly Ala Gly Ala Gly Ser Gly Val Gly Val Pro Gly
            820                 825                 830
Val Gly Val Pro Gly Val Gly Val Pro Gly Val Gly Val Pro Gly Lys
        835                 840                 845
Gly Val Pro Gly Val Gly Val Pro Gly Val Gly Val Pro Gly Val Gly
    850                 855                 860
Val Pro Gly Ala Gly Ala Gly Ser Gly Ala Gly Ala Gly Ser Gly Ala
865                 870                 875                 880
```

```
Gly Ala Gly Ser Gly Ala Gly Ser Gly Val Gly Val Pro Gly
            885                 890                 895

Val Gly Val Pro Gly Val Gly Val Pro Gly Val Gly Val Pro Gly Lys
            900                 905                 910

Gly Val Pro Gly Val Gly Val Pro Gly Val Gly Val Pro Gly Val Gly
            915                 920                 925

Val Pro Gly Ala Gly Ala Gly Ser Gly Ala Gly Ala Gly Ser Gly Ala
            930                 935                 940

Gly Ala Gly Ser Gly Ala Gly Ala Gly Ser Gly Val Gly Val Pro Gly
945                 950                 955                 960

Val Gly Val Pro Gly Val Gly Val Pro Gly Val Gly Val Pro Gly Lys
            965                 970                 975

Gly Val Pro Gly Val Gly Val Pro Gly Val Gly Val Pro Gly Val Gly
            980                 985                 990

Val Pro Gly Ala Gly Ala Gly Ser  Gly Ala Gly Ala Gly  Ser Gly Ala
            995                 1000                1005

Gly Ala  Met Asp Pro Gly Arg  Tyr Gln Asp Leu Arg  Ser His His
            1010                1015                1020

His His  His His
            1025

<210> SEQ ID NO 33
<211> LENGTH: 1105
<212> TYPE: PRT
<213> ORGANISM: unknown
<220> FEATURE:
<223> OTHER INFORMATION: silk, elastin and MBI peptide repeats

<400> SEQUENCE: 33

Met Asp Pro His Met Arg Ser Leu Val Pro Arg Gly Ser Gly Gly Gly
1               5                   10                  15

Gly Gly Gly Lys Trp Lys Leu Phe Lys Lys Ile Gly Ile Gly Ala Val
            20                  25                  30

Leu Lys Val Leu Thr Thr Gly Leu Pro Ala Leu Lys Leu Thr Lys Gly
        35                  40                  45

Gly Gly Gly Gly Gly Lys Trp Lys Leu Phe Lys Lys Ile Gly Ile Gly
    50                  55                  60

Ala Val Leu Lys Val Leu Thr Thr Gly Leu Pro Ala Leu Lys Leu Thr
65                  70                  75                  80

Lys Gly Gly Gly Gly Gly Gly Lys Trp Lys Leu Phe Lys Lys Ile Gly
                85                  90                  95

Ile Gly Ala Val Leu Lys Val Leu Thr Thr Gly Leu Pro Ala Leu Lys
            100                 105                 110

Leu Thr Lys Gly Gly Gly Gly Gly Gly Lys Trp Lys Leu Phe Lys Lys
        115                 120                 125

Ile Gly Ile Gly Ala Val Leu Lys Val Leu Thr Thr Gly Leu Pro Ala
    130                 135                 140

Leu Lys Leu Thr Lys Gly Gly Gly Gly Gly Gly Lys Trp Lys Leu Phe
145                 150                 155                 160

Lys Lys Ile Gly Ile Gly Ala Val Leu Lys Val Leu Thr Thr Gly Leu
                165                 170                 175

Pro Ala Leu Lys Leu Thr Lys Gly Gly Gly Gly Gly Gly Lys Trp Lys
            180                 185                 190

Leu Phe Lys Lys Ile Gly Ile Gly Ala Val Leu Lys Val Leu Thr Thr
        195                 200                 205
```

-continued

```
Gly Leu Pro Ala Leu Lys Leu Thr Lys Lys Ile Cys Ile Trp Asp Pro
    210                 215                 220

Val Val Leu Gln Arg Arg Asp Trp Glu Asn Pro Gly Val Thr Gln Leu
225                 230                 235                 240

Asn Arg Leu Ala Ala His Pro Pro Phe Ala Ser Asp Pro Met Gly Ala
                245                 250                 255

Gly Ser Gly Ala Gly Ala Gly Ser Gly Val Gly Val Pro Gly Val Gly
            260                 265                 270

Val Pro Gly Val Gly Val Pro Gly Val Gly Val Pro Gly Lys Gly Val
        275                 280                 285

Pro Gly Val Gly Val Pro Gly Val Gly Val Pro Gly Val Gly Val Pro
    290                 295                 300

Gly Ala Gly Ala Gly Ser Gly Ala Gly Ala Gly Ser Gly Ala Gly Ala
305                 310                 315                 320

Gly Ser Gly Ala Gly Ala Gly Ser Gly Val Gly Val Pro Gly Val Gly
                325                 330                 335

Val Pro Gly Val Gly Val Pro Gly Val Gly Val Pro Gly Lys Gly Val
            340                 345                 350

Pro Gly Val Gly Val Pro Gly Val Gly Val Pro Gly Val Gly Val Pro
        355                 360                 365

Gly Ala Gly Ala Gly Ser Gly Ala Gly Ala Gly Ser Gly Ala Gly Ala
    370                 375                 380

Gly Ser Gly Ala Gly Ala Gly Ser Gly Val Gly Val Pro Gly Val Gly
385                 390                 395                 400

Val Pro Gly Val Gly Val Pro Gly Val Gly Val Pro Gly Lys Gly Val
                405                 410                 415

Pro Gly Val Gly Val Pro Gly Val Gly Val Pro Gly Val Gly Val Pro
            420                 425                 430

Gly Ala Gly Ala Gly Ser Gly Ala Gly Ala Gly Ser Gly Ala Gly Ala
        435                 440                 445

Gly Ser Gly Ala Gly Ala Gly Ser Gly Val Gly Val Pro Gly Val Gly
    450                 455                 460

Val Pro Gly Val Gly Val Pro Gly Val Gly Val Pro Gly Lys Gly Val
465                 470                 475                 480

Pro Gly Val Gly Val Pro Gly Val Gly Val Pro Gly Val Gly Val Pro
                485                 490                 495

Gly Ala Gly Ala Gly Ser Gly Ala Gly Ala Gly Ser Gly Ala Gly Ala
            500                 505                 510

Gly Ser Gly Ala Gly Ala Gly Ser Gly Val Gly Val Pro Gly Val Gly
        515                 520                 525

Val Pro Gly Val Gly Val Pro Gly Val Gly Val Pro Gly Lys Gly Val
    530                 535                 540

Pro Gly Val Gly Val Pro Gly Val Gly Val Pro Gly Val Gly Val Pro
545                 550                 555                 560

Gly Ala Gly Ala Gly Ser Gly Ala Gly Ala Gly Ser Gly Ala Gly Ala
                565                 570                 575

Gly Ser Gly Ala Gly Ala Gly Ser Gly Val Gly Val Pro Gly Val Gly
            580                 585                 590

Val Pro Gly Val Gly Val Pro Gly Val Gly Val Pro Gly Lys Gly Val
        595                 600                 605

Pro Gly Val Gly Val Pro Gly Val Gly Val Pro Gly Val Gly Val Pro
    610                 615                 620
```

-continued

```
Gly Ala Gly Ala Gly Ser Gly Ala Gly Ala Gly Ser Gly Ala Gly Ala
625                 630                 635                 640
Gly Ser Gly Ala Gly Ala Gly Ser Gly Val Gly Val Pro Gly Val Gly
            645                 650                 655
Val Pro Gly Val Gly Val Pro Gly Val Gly Val Pro Gly Lys Gly Val
                660                 665                 670
Pro Gly Val Gly Val Pro Gly Val Gly Val Pro Gly Val Gly Val Pro
            675                 680                 685
Gly Ala Gly Ala Gly Ser Gly Ala Gly Ala Gly Ser Gly Ala Gly Ala
        690                 695                 700
Gly Ser Gly Ala Gly Ala Gly Ser Gly Val Gly Val Pro Gly Val Gly
705                 710                 715                 720
Val Pro Gly Val Gly Val Pro Gly Val Gly Val Pro Gly Lys Gly Val
                725                 730                 735
Pro Gly Val Gly Val Pro Gly Val Gly Val Pro Gly Val Gly Val Pro
            740                 745                 750
Gly Ala Gly Ala Gly Ser Gly Ala Gly Ala Gly Ser Gly Ala Gly Ala
        755                 760                 765
Gly Ser Gly Ala Gly Ala Gly Ser Gly Val Gly Val Pro Gly Val Gly
770                 775                 780
Val Pro Gly Val Gly Val Pro Gly Val Gly Val Pro Gly Lys Gly Val
785                 790                 795                 800
Pro Gly Val Gly Val Pro Gly Val Gly Val Pro Gly Val Gly Val Pro
            805                 810                 815
Gly Ala Gly Ala Gly Ser Gly Ala Gly Ala Gly Ser Gly Ala Gly Ala
            820                 825                 830
Gly Ser Gly Ala Gly Ala Gly Ser Gly Val Gly Val Pro Gly Val Gly
        835                 840                 845
Val Pro Gly Val Gly Val Pro Gly Val Gly Val Pro Gly Lys Gly Val
            850                 855                 860
Pro Gly Val Gly Val Pro Gly Val Gly Val Pro Gly Val Gly Val Pro
865                 870                 875                 880
Gly Ala Gly Ala Gly Ser Gly Ala Gly Ala Gly Ser Gly Ala Gly Ala
                885                 890                 895
Gly Ser Gly Ala Gly Ala Gly Ser Gly Val Gly Val Pro Gly Val Gly
            900                 905                 910
Val Pro Gly Val Gly Val Pro Gly Val Gly Val Pro Gly Lys Gly Val
            915                 920                 925
Pro Gly Val Gly Val Pro Gly Val Gly Val Pro Gly Val Gly Val Pro
        930                 935                 940
Gly Ala Gly Ala Gly Ser Gly Ala Gly Ala Gly Ser Gly Ala Gly Ala
945                 950                 955                 960
Gly Ser Gly Ala Gly Ala Gly Ser Gly Val Gly Val Pro Gly Val Gly
            965                 970                 975
Val Pro Gly Val Gly Val Pro Gly Val Gly Val Pro Gly Lys Gly Val
                980                 985                 990
Pro Gly Val Gly Val Pro Gly Val  Gly Val Pro Gly Val  Gly Val Pro
            995                 1000                1005
Gly Ala  Gly Ala Gly Ser Gly  Ala Gly Ala Gly Ser  Gly Ala Gly
        1010                1015                1020
Ala Gly  Ser Gly Ala Gly Ala  Gly Ser Gly Val Gly  Val Pro Gly
        1025                1030                1035
Val Gly  Val Pro Gly Val Gly  Val Pro Gly Val Gly  Val Pro Gly
```

-continued

```
                1040                1045                1050

Lys Gly Val Pro Gly Val Val Pro Gly Val Gly  Val Pro Gly
    1055                1060                1065

Val Gly Val Pro Gly Ala Gly  Ala Gly Ser Gly Ala  Gly Ala Gly
    1070                1075                1080

Ser Gly Ala Gly Ala Met Asp  Pro Gly Arg Tyr Gln  Asp Leu Arg
    1085                1090                1095

Ser His  His His His His
    1100                1105

<210> SEQ ID NO 34
<211> LENGTH: 1125
<212> TYPE: PRT
<213> ORGANISM: unknown
<220> FEATURE:
<223> OTHER INFORMATION: GFP-SELP47K: silk, elastin and green
      fluorescent protein peptides

<400> SEQUENCE: 34

Met Asp Pro Met Ser Lys Gly Glu Glu Leu Phe Thr Gly Val Val Pro
1               5                   10                  15

Ile Leu Val Glu Leu Asp Gly Asp Val Asn Gly His Lys Phe Ser Val
            20                  25                  30

Ser Gly Glu Gly Glu Gly Asp Ala Thr Tyr Gly Lys Leu Thr Leu Lys
        35                  40                  45

Phe Ile Cys Thr Thr Gly Lys Leu Pro Val Pro Trp Pro Thr Leu Val
    50                  55                  60

Thr Thr Phe Ser Tyr Gly Val Gln Cys Phe Ser Arg Tyr Pro Asp His
65                  70                  75                  80

Met Lys Arg His Asp Phe Phe Lys Ser Ala Met Pro Glu Gly Tyr Val
                85                  90                  95

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
        115                 120                 125

Lys Gly Ile Asp Phe Lys Glu Asp Gly Asn Ile Leu Gly His Lys Leu
    130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
        195                 200                 205

Ala Leu Ser Lys Asp Pro Asn Glu Lys Arg Asp His Met Val Leu Leu
    210                 215                 220

Glu Phe Val Thr Ala Ala Gly Ile Thr His Gly Met Asp Glu Leu Tyr
225                 230                 235                 240

Lys Ala Asp Pro Val Val Leu Gln Arg Arg Asp Trp Glu Asn Pro Gly
                245                 250                 255

Val Thr Gln Leu Asn Arg Leu Ala Ala His Pro Pro Phe Ala Ser Asp
            260                 265                 270

Pro Met Gly Ala Gly Ser Gly Ala Gly Ala Gly Ser Gly Val Gly Val
        275                 280                 285
```

-continued

```
Pro Gly Val Gly Val Pro Gly Val Gly Val Pro Gly Val Gly Val Pro
    290                 295                 300
Gly Lys Gly Val Pro Gly Val Gly Val Pro Gly Val Gly Val Pro Gly
305                 310                 315                 320
Val Gly Val Pro Gly Ala Gly Ala Gly Ser Gly Ala Gly Ala Gly Ser
                325                 330                 335
Gly Ala Gly Ala Gly Ser Gly Ala Gly Ala Gly Ser Gly Val Gly Val
            340                 345                 350
Pro Gly Val Gly Val Pro Gly Val Gly Val Pro Gly Val Gly Val Pro
        355                 360                 365
Gly Lys Gly Val Pro Gly Val Gly Val Pro Gly Val Gly Val Pro Gly
    370                 375                 380
Val Gly Val Pro Gly Ala Gly Ala Gly Ser Gly Ala Gly Ala Gly Ser
385                 390                 395                 400
Gly Ala Gly Ala Gly Ser Gly Ala Gly Ala Gly Ser Gly Val Gly Val
                405                 410                 415
Pro Gly Val Gly Val Pro Gly Val Gly Val Pro Gly Val Gly Val Pro
            420                 425                 430
Gly Lys Gly Val Pro Gly Val Gly Val Pro Gly Val Gly Val Pro Gly
        435                 440                 445
Val Gly Val Pro Gly Ala Gly Ala Gly Ser Gly Ala Gly Ala Gly Ser
    450                 455                 460
Gly Ala Gly Ala Gly Ser Gly Ala Gly Ala Gly Ser Gly Val Gly Val
465                 470                 475                 480
Pro Gly Val Gly Val Pro Gly Val Gly Val Pro Gly Val Gly Val Pro
                485                 490                 495
Gly Lys Gly Val Pro Gly Val Gly Val Pro Gly Val Gly Val Pro Gly
            500                 505                 510
Val Gly Val Pro Gly Ala Gly Ala Gly Ser Gly Ala Gly Ala Gly Ser
        515                 520                 525
Gly Ala Gly Ala Gly Ser Gly Ala Gly Ala Gly Ser Gly Val Gly Val
    530                 535                 540
Pro Gly Val Gly Val Pro Gly Val Gly Val Pro Gly Val Gly Val Pro
545                 550                 555                 560
Gly Lys Gly Val Pro Gly Val Gly Val Pro Gly Val Gly Val Pro Gly
                565                 570                 575
Val Gly Val Pro Gly Ala Gly Ala Gly Ser Gly Ala Gly Ala Gly Ser
            580                 585                 590
Gly Ala Gly Ala Gly Ser Gly Ala Gly Ala Gly Ser Gly Val Gly Val
        595                 600                 605
Pro Gly Val Gly Val Pro Gly Val Gly Val Pro Gly Val Gly Val Pro
    610                 615                 620
Gly Lys Gly Val Pro Gly Val Gly Val Pro Gly Val Gly Val Pro Gly
625                 630                 635                 640
Val Gly Val Pro Gly Ala Gly Ala Gly Ser Gly Ala Gly Ala Gly Ser
                645                 650                 655
Gly Ala Gly Ala Gly Ser Gly Ala Gly Ala Gly Ser Gly Val Gly Val
            660                 665                 670
Pro Gly Val Gly Val Pro Gly Val Gly Val Pro Gly Val Gly Val Pro
        675                 680                 685
Gly Lys Gly Val Pro Gly Val Gly Val Pro Gly Val Gly Val Pro Gly
    690                 695                 700
Val Gly Val Pro Gly Ala Gly Ala Gly Ser Gly Ala Gly Ala Gly Ser
```

-continued

```
            705                 710                 715                 720
Gly Ala Gly Ala Gly Ser Gly Ala Gly Ala Ser Gly Val Gly Val
                725                 730                 735
Pro Gly Val Gly Val Pro Gly Val Gly Val Pro Gly Val Gly Val Pro
                740                 745                 750
Gly Lys Gly Val Pro Gly Val Gly Val Pro Gly Val Gly Val Pro Gly
                755                 760                 765
Val Gly Val Pro Gly Ala Gly Ala Ser Gly Ala Gly Ala Gly Ser
            770                 775                 780
Gly Ala Gly Ala Gly Ser Gly Ala Gly Ala Ser Gly Val Gly Val
785                 790                 795                 800
Pro Gly Val Gly Val Pro Gly Val Gly Val Pro Gly Val Gly Val Pro
                805                 810                 815
Gly Lys Gly Val Pro Gly Val Gly Val Pro Gly Val Gly Val Pro Gly
                820                 825                 830
Val Gly Val Pro Gly Ala Gly Ala Ser Gly Ala Gly Ala Gly Ser
            835                 840                 845
Gly Ala Gly Ala Gly Ser Gly Ala Gly Ala Ser Gly Val Gly Val
850                 855                 860
Pro Gly Val Gly Val Pro Gly Val Gly Val Pro Gly Val Gly Val Pro
865                 870                 875                 880
Gly Lys Gly Val Pro Gly Val Gly Val Pro Gly Val Gly Val Pro Gly
                885                 890                 895
Val Gly Val Pro Gly Ala Gly Ala Ser Gly Ala Gly Ala Gly Ser
            900                 905                 910
Gly Ala Gly Ala Gly Ser Gly Ala Gly Ala Ser Gly Val Gly Val
            915                 920                 925
Pro Gly Val Gly Val Pro Gly Val Gly Val Pro Gly Val Gly Val Pro
            930                 935                 940
Gly Lys Gly Val Pro Gly Val Gly Val Pro Gly Val Gly Val Pro Gly
945                 950                 955                 960
Val Gly Val Pro Gly Ala Gly Ala Ser Gly Ala Gly Ala Gly Ser
                965                 970                 975
Gly Ala Gly Ala Gly Ser Gly Ala Gly Ala Ser Gly Val Gly Val
            980                 985                 990
Pro Gly Val Gly Val Pro Gly Val  Gly Val Pro Gly Val  Gly Val Pro
            995                 1000                1005
Gly Lys  Gly Val Pro Gly Val  Gly Val Pro Gly Val  Gly Val Pro
    1010                1015                1020
Gly Val  Gly Val Pro Gly Ala  Gly Ala Gly Ser Gly  Ala Gly Ala
    1025                1030                1035
Gly Ser  Gly Ala Gly Ala Gly  Ser Gly Ala Gly Ala  Gly Ser Gly
    1040                1045                1050
Val Gly  Val Pro Gly Val Gly  Val Pro Gly Val Gly  Val Pro Gly
    1055                1060                1065
Val Gly  Val Pro Gly Lys Gly  Val Pro Gly Val Gly  Val Pro Gly
    1070                1075                1080
Val Gly  Val Pro Gly Val Gly  Val Pro Gly Ala Gly  Ala Gly Ser
    1085                1090                1095
Gly Ala  Gly Ala Gly Ser Gly  Ala Gly Ala Met Asp  Pro Gly Arg
    1100                1105                1110
Tyr Gln  Asp Leu Arg Ser His  His His His His
    1115                1120                1125
```

```
<210> SEQ ID NO 35
<211> LENGTH: 1043
<212> TYPE: PRT
<213> ORGANISM: unknown
<220> FEATURE:
<223> OTHER INFORMATION: CBP-SELP47K-S2E1

<400> SEQUENCE: 35

His Met Asp Pro Val Leu Gln Arg Arg Asp Trp Glu Asn Pro Gly
1               5                   10                  15

Val Thr Gln Leu Asn Arg Leu Ala Ala His Pro Pro Phe Ala Ser Asp
            20                  25                  30

Pro Met Gly Ala Gly Ala Gly Ser Gly Ala Gly Ala Gly Ser Thr Thr
        35                  40                  45

His Pro Gln Met Leu Trp Gln Met Ser Thr Gly Val Gly Val Pro Gly
    50                  55                  60

Val Gly Val Pro Gly Val Gly Val Pro Gly Val Gly Val Pro Gly Lys
65                  70                  75                  80

Gly Val Pro Gly Val Gly Val Pro Gly Val Gly Val Pro Gly Val Gly
                85                  90                  95

Val Pro Gly Ala Gly Ala Gly Ser Gly Ala Gly Ala Gly Ser Gly Ala
            100                 105                 110

Gly Ala Gly Ser Gly Ala Gly Ala Gly Ser Thr Thr His Pro Gln Met
        115                 120                 125

Leu Trp Gln Met Ser Thr Gly Val Gly Val Pro Gly Val Gly Val Pro
    130                 135                 140

Gly Val Gly Val Pro Gly Val Gly Val Pro Gly Lys Gly Val Pro Gly
145                 150                 155                 160

Val Gly Val Pro Gly Val Gly Val Pro Gly Val Gly Val Pro Gly Ala
                165                 170                 175

Gly Ala Gly Ser Gly Ala Gly Ala Gly Ser Gly Ala Gly Ala Gly Ser
            180                 185                 190

Gly Ala Gly Ala Gly Ser Thr Thr His Pro Gln Met Leu Trp Gln Met
        195                 200                 205

Ser Thr Gly Val Gly Val Pro Gly Val Gly Val Pro Gly Val Gly Val
    210                 215                 220

Pro Gly Val Gly Val Pro Gly Lys Gly Val Pro Gly Val Gly Val Pro
225                 230                 235                 240

Gly Val Gly Val Pro Gly Val Gly Val Pro Gly Ala Gly Ala Gly Ser
                245                 250                 255

Gly Ala Gly Ala Gly Ser Gly Ala Gly Ala Gly Ser Gly Ala Gly Ala
            260                 265                 270

Gly Ser Thr Thr His Pro Gln Met Leu Trp Gln Met Ser Thr Gly Val
        275                 280                 285

Gly Val Pro Gly Val Gly Val Pro Gly Val Gly Val Pro Gly Val Gly
    290                 295                 300

Val Pro Gly Lys Gly Val Pro Gly Val Gly Val Pro Gly Val Gly Val
305                 310                 315                 320

Pro Gly Val Gly Val Pro Gly Ala Gly Ala Gly Ser Gly Ala Gly Ala
                325                 330                 335

Gly Ser Gly Ala Gly Ala Gly Ser Gly Ala Gly Ala Gly Ser Thr Thr
            340                 345                 350

His Pro Gln Met Leu Trp Gln Met Ser Thr Gly Val Gly Val Pro Gly
        355                 360                 365
```

-continued

```
Val Gly Val Pro Gly Val Gly Val Pro Gly Val Gly Val Pro Gly Lys
        370                 375                 380
Gly Val Pro Gly Val Gly Val Pro Gly Val Gly Val Pro Gly Val Gly
385                 390                 395                 400
Val Pro Gly Ala Gly Ala Gly Ser Gly Ala Gly Ser Gly Ala
                405                 410                 415
Gly Ala Gly Ser Gly Ala Gly Ala Gly Ser Thr Thr His Pro Gln Met
                420                 425                 430
Leu Trp Gln Met Ser Thr Gly Val Gly Val Pro Gly Val Gly Val Pro
                435                 440                 445
Gly Val Gly Val Pro Gly Val Gly Val Pro Gly Lys Gly Val Pro Gly
        450                 455                 460
Val Gly Val Pro Gly Val Gly Val Pro Gly Val Gly Val Pro Gly Ala
465                 470                 475                 480
Gly Ala Gly Ser Gly Ala Gly Ala Gly Ser Gly Ala Gly Ala Gly Ser
                485                 490                 495
Gly Ala Gly Ala Gly Ser Thr Thr His Pro Gln Met Leu Trp Gln Met
                500                 505                 510
Ser Thr Gly Val Gly Val Pro Gly Val Gly Val Pro Gly Val Gly Val
        515                 520                 525
Pro Gly Val Gly Val Pro Gly Lys Gly Val Pro Gly Val Gly Val Pro
        530                 535                 540
Gly Val Gly Val Pro Gly Val Gly Val Pro Gly Ala Gly Ala Gly Ser
545                 550                 555                 560
Gly Ala Gly Ala Gly Ser Gly Ala Gly Ala Gly Ser Gly Ala Gly Ala
                565                 570                 575
Gly Ser Thr Thr His Pro Gln Met Leu Trp Gln Met Ser Thr Gly Val
                580                 585                 590
Gly Val Pro Gly Val Gly Val Pro Gly Val Gly Val Pro Gly Val Gly
        595                 600                 605
Val Pro Gly Lys Gly Val Pro Gly Val Gly Val Pro Gly Val Gly Val
        610                 615                 620
Pro Gly Val Gly Val Pro Gly Ala Gly Ala Gly Ser Gly Ala Gly Ala
625                 630                 635                 640
Gly Ser Gly Ala Gly Ala Gly Ser Gly Ala Gly Ala Gly Ser Thr Thr
                645                 650                 655
His Pro Gln Met Leu Trp Gln Met Ser Thr Gly Val Gly Val Pro Gly
                660                 665                 670
Val Gly Val Pro Gly Val Gly Val Pro Gly Val Gly Val Pro Gly Lys
        675                 680                 685
Gly Val Pro Gly Val Gly Val Pro Gly Val Gly Val Pro Gly Val Gly
        690                 695                 700
Val Pro Gly Ala Gly Ala Gly Ser Gly Ala Gly Ala Gly Ser Gly Ala
705                 710                 715                 720
Gly Ala Gly Ser Gly Ala Gly Ala Gly Ser Thr Thr His Pro Gln Met
                725                 730                 735
Leu Trp Gln Met Ser Thr Gly Val Gly Val Pro Gly Val Gly Val Pro
                740                 745                 750
Gly Val Gly Val Pro Gly Val Gly Val Pro Gly Lys Gly Val Pro Gly
        755                 760                 765
Val Gly Val Pro Gly Val Gly Val Pro Gly Val Gly Val Pro Gly Ala
        770                 775                 780
```

```
Gly Ala Gly Ser Gly Ala Gly Ser Gly Ala Gly Ala Gly Ser
785                 790                 795                 800

Gly Ala Gly Ala Gly Ser Thr Thr His Pro Gln Met Leu Trp Gln Met
                805                 810                 815

Ser Thr Gly Val Gly Val Pro Gly Val Gly Val Pro Gly Val Gly Val
            820                 825                 830

Pro Gly Val Gly Val Pro Gly Lys Gly Val Pro Gly Val Gly Val Pro
        835                 840                 845

Gly Val Gly Val Pro Gly Val Gly Val Pro Gly Ala Gly Ala Gly Ser
        850                 855                 860

Gly Ala Gly Ala Gly Ser Gly Ala Ala Gly Ser Gly Ala Gly Ala
865                 870                 875                 880

Gly Ser Thr Thr His Pro Gln Met Leu Trp Gln Met Ser Thr Gly Val
                885                 890                 895

Gly Val Pro Gly Val Gly Val Pro Gly Val Gly Val Pro Gly Val Gly
            900                 905                 910

Val Pro Gly Lys Gly Val Pro Gly Val Gly Val Pro Gly Val Gly Val
        915                 920                 925

Pro Gly Val Gly Val Pro Gly Ala Gly Ala Gly Ser Gly Ala Gly Ala
        930                 935                 940

Gly Ser Gly Ala Gly Ala Gly Ser Gly Ala Gly Ala Gly Ser Thr Thr
945                 950                 955                 960

His Pro Gln Met Leu Trp Gln Met Ser Thr Gly Val Gly Val Pro Gly
                965                 970                 975

Val Gly Val Pro Gly Val Gly Val Pro Gly Val Gly Val Pro Gly Lys
            980                 985                 990

Gly Val Pro Gly Val Gly Val Pro  Gly Val Gly Val Pro  Gly Val Gly
        995                 1000                1005

Val Pro  Gly Ala Gly Ala Gly  Ser Gly Ala Gly Ala  Gly Ser Gly
    1010                1015                1020

Ala Gly  Ala Met Asp Pro Gly  Arg Tyr Gln Asp Leu  Arg Ser His
    1025                1030                1035

His His  His His His
    1040

<210> SEQ ID NO 36
<211> LENGTH: 1016
<212> TYPE: PRT
<213> ORGANISM: unknown
<220> FEATURE:
<223> OTHER INFORMATION: P4-SELP47K:  silk, elastin ad UV-protective
      peptides

<400> SEQUENCE: 36

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
                20                  25                  30

Met Gly Ala Gly Ala Gly Ser Gly Ala Gly Ala Gly Ser Ala Leu Ser
            35                  40                  45

Tyr Pro Gly Val Gly Val Pro Gly Val Gly Val Pro Gly Val Gly Val
        50                  55                  60

Pro Gly Val Gly Val Pro Gly Lys Gly Val Pro Gly Val Gly Val Pro
65                  70                  75                  80

Gly Val Gly Val Pro Gly Val Gly Val Pro Ala Leu Ser Tyr Pro Gly
                85                  90                  95
```

```
Ala Gly Ala Gly Ser Gly Ala Gly Ser Gly Ala Gly
            100                 105                 110

Ser Gly Ala Gly Ala Gly Ser Ala Leu Ser Tyr Pro Gly Val Gly Val
            115                 120                 125

Pro Gly Val Gly Val Pro Gly Val Gly Val Pro Gly Val Gly Val Pro
            130                 135                 140

Gly Lys Gly Val Pro Gly Val Gly Val Pro Gly Val Gly Val Pro Gly
145                 150                 155                 160

Val Gly Val Pro Ala Leu Ser Tyr Pro Gly Ala Gly Ala Gly Ser Gly
                165                 170                 175

Ala Gly Ala Gly Ser Gly Ala Gly Ser Gly Ala Gly
            180                 185                 190

Ser Ala Leu Ser Tyr Pro Gly Val Gly Val Pro Gly Val Gly Val Pro
            195                 200                 205

Gly Val Gly Val Pro Gly Val Gly Val Pro Gly Lys Gly Val Pro Gly
            210                 215                 220

Val Gly Val Pro Gly Val Gly Val Pro Gly Val Gly Val Pro Ala Leu
225                 230                 235                 240

Ser Tyr Pro Gly Ala Gly Ala Gly Ser Gly Ala Gly Ala Gly Ser Gly
                245                 250                 255

Ala Gly Ala Gly Ser Gly Ala Gly Ser Ala Leu Ser Tyr Pro
            260                 265                 270

Gly Val Gly Val Pro Gly Val Gly Val Pro Gly Val Gly Val Pro Gly
            275                 280                 285

Val Gly Val Pro Gly Lys Gly Val Pro Gly Val Gly Val Pro Gly Val
    290                 295                 300

Gly Val Pro Gly Val Gly Val Pro Ala Leu Ser Tyr Pro Gly Ala Gly
305                 310                 315                 320

Ala Gly Ser Gly Ala Gly Ala Gly Ser Gly Ala Gly Ala Gly Ser Gly
                325                 330                 335

Ala Gly Ala Gly Ser Ala Leu Ser Tyr Pro Gly Val Gly Val Pro Gly
            340                 345                 350

Val Gly Val Pro Gly Val Gly Val Pro Gly Val Gly Val Pro Gly Lys
            355                 360                 365

Gly Val Pro Gly Val Gly Val Pro Gly Val Gly Val Pro Gly Val Gly
            370                 375                 380

Val Pro Ala Leu Ser Tyr Pro Gly Ala Gly Ala Gly Ser Gly Ala Gly
385                 390                 395                 400

Ala Gly Ser Gly Ala Gly Ala Gly Ser Gly Ala Gly Ala Gly Ser Ala
                405                 410                 415

Leu Ser Tyr Pro Gly Val Gly Val Pro Gly Val Gly Val Pro Gly Val
            420                 425                 430

Gly Val Pro Gly Val Gly Val Pro Gly Lys Gly Val Pro Gly Val Gly
            435                 440                 445

Val Pro Gly Val Gly Val Pro Gly Val Gly Val Pro Ala Leu Ser Tyr
    450                 455                 460

Pro Gly Ala Gly Ala Gly Ser Gly Ala Gly Ala Gly Ser Gly Ala Gly
465                 470                 475                 480

Ala Gly Ser Gly Ala Gly Ala Gly Ser Ala Leu Ser Tyr Pro Gly Val
                485                 490                 495

Gly Val Pro Gly Val Gly Val Pro Gly Val Gly Val Pro Gly Val Gly
            500                 505                 510
```

-continued

```
Val Pro Gly Lys Gly Val Pro Gly Val Gly Val Pro Gly Val Gly Val
            515                 520                 525
Pro Gly Val Gly Val Pro Ala Leu Ser Tyr Pro Gly Ala Gly Ala Gly
            530                 535                 540
Ser Gly Ala Gly Ala Gly Ser Gly Ala Gly Ala Gly Ser Gly Ala Gly
545                 550                 555                 560
Ala Gly Ser Ala Leu Ser Tyr Pro Gly Val Gly Val Pro Gly Val Gly
            565                 570                 575
Val Pro Gly Val Gly Val Pro Gly Val Gly Val Pro Gly Lys Gly Val
            580                 585                 590
Pro Gly Val Gly Val Pro Gly Val Gly Val Pro Gly Val Gly Val Pro
            595                 600                 605
Ala Leu Ser Tyr Pro Gly Ala Gly Ala Gly Ser Gly Ala Gly Ala Gly
            610                 615                 620
Ser Gly Ala Gly Ala Gly Ser Gly Ala Gly Ala Gly Ser Ala Leu Ser
625                 630                 635                 640
Tyr Pro Gly Val Gly Val Pro Gly Val Gly Val Pro Gly Val Gly Val
            645                 650                 655
Pro Gly Val Gly Val Pro Gly Lys Gly Val Pro Gly Val Gly Val Pro
            660                 665                 670
Gly Val Gly Val Pro Gly Val Gly Val Pro Ala Leu Ser Tyr Pro Gly
            675                 680                 685
Ala Gly Ala Gly Ser Gly Ala Gly Ala Gly Ser Gly Ala Gly Ala Gly
            690                 695                 700
Ser Gly Ala Gly Ala Gly Ser Ala Leu Ser Tyr Pro Gly Val Gly Val
705                 710                 715                 720
Pro Gly Val Gly Val Pro Gly Val Gly Val Pro Gly Val Gly Val Pro
            725                 730                 735
Gly Lys Gly Val Pro Gly Val Gly Val Pro Gly Val Gly Val Pro Gly
            740                 745                 750
Val Gly Val Pro Ala Leu Ser Tyr Pro Gly Ala Gly Ala Gly Ser Gly
            755                 760                 765
Ala Gly Ala Gly Ser Gly Ala Gly Ala Gly Ser Gly Ala Gly Ala Gly
            770                 775                 780
Ser Ala Leu Ser Tyr Pro Gly Val Gly Val Pro Gly Val Gly Val Pro
785                 790                 795                 800
Gly Val Gly Val Pro Gly Val Gly Val Pro Gly Lys Gly Val Pro Gly
            805                 810                 815
Val Gly Val Pro Gly Val Gly Val Pro Gly Val Gly Val Pro Ala Leu
            820                 825                 830
Ser Tyr Pro Gly Ala Gly Ala Gly Ser Gly Ala Gly Ala Gly Ser Gly
            835                 840                 845
Ala Gly Ala Gly Ser Gly Ala Gly Ala Gly Ser Ala Leu Ser Tyr Pro
            850                 855                 860
Gly Val Gly Val Pro Gly Val Gly Val Pro Gly Val Gly Val Pro Gly
865                 870                 875                 880
Val Gly Val Pro Gly Lys Gly Val Pro Gly Val Gly Val Pro Gly Val
            885                 890                 895
Gly Val Pro Gly Val Gly Val Pro Ala Leu Ser Tyr Pro Gly Ala Gly
            900                 905                 910
Ala Gly Ser Gly Ala Gly Ala Gly Ser Gly Ala Gly Ala Gly Ser Gly
            915                 920                 925
Ala Gly Ala Gly Ser Ala Leu Ser Tyr Pro Gly Val Gly Val Pro Gly
```

-continued 930              935              940
Val Gly Val Pro Gly Val Gly Val Pro Gly Val Gly Val Pro Gly Lys
945                  950                  955                  960

Gly Val Pro Gly Val Gly Val Pro Gly Val Gly Val Pro Gly Val Gly
                 965                  970                  975

Val Pro Ala Leu Ser Tyr Pro Gly Ala Gly Ala Gly Ser Gly Ala Gly
             980                  985                  990

Ala Gly Ser Gly Ala Gly Ala Met Asp Pro Gly Arg Tyr Gln Asp Leu
         995                 1000                 1005

Arg Ser His His His His His His
    1010                 1015

<210> SEQ ID NO 37
<211> LENGTH: 983
<212> TYPE: PRT
<213> ORGANISM: unknown
<220> FEATURE:
<223> OTHER INFORMATION: CBPhexamer-SELP47K: silk, elastin and
      cellulose binding peptide protein polymer sequence

<400> SEQUENCE: 37

Met Asp Pro Thr Thr His Pro Gln Met Leu Trp Gln Met Ser Thr Gly
1               5                   10                  15

Gly Gly Gly Thr Thr His Pro Gln Met Leu Trp Gln Met Ser Thr Gly
            20                  25                  30

Gly Gly Gly Thr Thr His Pro Gln Met Leu Trp Gln Met Ser Thr Gly
        35                  40                  45

Gly Gly Gly Thr Thr His Pro Gln Met Leu Trp Gln Met Ser Thr Gly
    50                  55                  60

Gly Gly Gly Thr Thr His Pro Gln Met Leu Trp Gln Met Ser Thr Gly
65                  70                  75                  80

Gly Gly Gly Thr Thr His Pro Gln Met Leu Trp Gln Met Ser Thr Gly
                85                  90                  95

Gly Gly Gly Ala Asp Pro Val Val Leu Gln Arg Arg Asp Trp Glu Asn
            100                 105                 110

Pro Gly Val Thr Gln Leu Asn Arg Leu Ala Ala His Pro Pro Phe Ala
        115                 120                 125

Ser Asp Pro Met Gly Ala Gly Ser Gly Ala Gly Ala Gly Ser Gly Val
    130                 135                 140

Gly Val Pro Gly Val Gly Val Pro Gly Val Gly Val Pro Gly Val Gly
145                 150                 155                 160

Val Pro Gly Lys Gly Val Pro Gly Val Gly Val Pro Gly Val Gly Val
                165                 170                 175

Pro Gly Val Gly Val Pro Gly Ala Gly Ala Gly Ser Gly Ala Gly Ala
            180                 185                 190

Gly Ser Gly Ala Gly Ala Gly Ser Gly Ala Gly Ala Gly Ser Gly Val
        195                 200                 205

Gly Val Pro Gly Val Gly Val Pro Gly Val Gly Val Pro Gly Val Gly
    210                 215                 220

Val Pro Gly Lys Gly Val Pro Gly Val Gly Val Pro Gly Val Gly Val
225                 230                 235                 240

Pro Gly Val Gly Val Pro Gly Ala Gly Ala Gly Ser Gly Ala Gly Ala
                245                 250                 255

Gly Ser Gly Ala Gly Ala Gly Ser Gly Ala Gly Ala Gly Ser Gly Val
            260                 265                 270

-continued

```
Gly Val Pro Gly Val Gly Val Pro Gly Val Gly Val Pro Gly Val Gly
            275                 280                 285
Val Pro Gly Lys Gly Val Pro Gly Val Gly Val Pro Gly Val Gly Val
            290                 295                 300
Pro Gly Val Gly Val Pro Gly Ala Gly Ala Gly Ser Gly Ala Gly Ala
305                 310                 315                 320
Gly Ser Gly Ala Gly Ala Gly Ser Gly Ala Gly Ala Gly Ser Gly Val
            325                 330                 335
Gly Val Pro Gly Val Gly Val Pro Gly Val Gly Val Pro Gly Val Gly
            340                 345                 350
Val Pro Gly Lys Gly Val Pro Gly Val Gly Val Pro Gly Val Gly Val
            355                 360                 365
Pro Gly Val Gly Val Pro Gly Ala Gly Ala Gly Ser Gly Ala Gly Ala
            370                 375                 380
Gly Ser Gly Ala Gly Ala Gly Ser Gly Ala Gly Ala Gly Ser Gly Val
385                 390                 395                 400
Gly Val Pro Gly Val Gly Val Pro Gly Val Gly Val Pro Gly Val Gly
            405                 410                 415
Val Pro Gly Lys Gly Val Pro Gly Val Gly Val Pro Gly Val Gly Val
            420                 425                 430
Pro Gly Val Gly Val Pro Gly Ala Gly Ala Gly Ser Gly Ala Gly Ala
            435                 440                 445
Gly Ser Gly Ala Gly Ala Gly Ser Gly Ala Gly Ala Gly Ser Gly Val
            450                 455                 460
Gly Val Pro Gly Val Gly Val Pro Gly Val Gly Val Pro Gly Val Gly
465                 470                 475                 480
Val Pro Gly Lys Gly Val Pro Gly Val Gly Val Pro Gly Val Gly Val
            485                 490                 495
Pro Gly Val Gly Val Pro Gly Ala Gly Ala Gly Ser Gly Ala Gly Ala
            500                 505                 510
Gly Ser Gly Ala Gly Ala Gly Ser Gly Ala Gly Ala Gly Ser Gly Val
            515                 520                 525
Gly Val Pro Gly Val Gly Val Pro Gly Val Gly Val Pro Gly Val Gly
            530                 535                 540
Val Pro Gly Lys Gly Val Pro Gly Val Gly Val Pro Gly Val Gly Val
545                 550                 555                 560
Pro Gly Val Gly Val Pro Gly Ala Gly Ala Gly Ser Gly Ala Gly Ala
            565                 570                 575
Gly Ser Gly Ala Gly Ala Gly Ser Gly Ala Gly Ala Gly Ser Gly Val
            580                 585                 590
Gly Val Pro Gly Val Gly Val Pro Gly Val Gly Val Pro Gly Val Gly
            595                 600                 605
Val Pro Gly Lys Gly Val Pro Gly Val Gly Val Pro Gly Val Gly Val
            610                 615                 620
Pro Gly Val Gly Val Pro Gly Ala Gly Ala Gly Ser Gly Ala Gly Ala
625                 630                 635                 640
Gly Ser Gly Ala Gly Ala Gly Ser Gly Ala Gly Ala Gly Ser Gly Val
            645                 650                 655
Gly Val Pro Gly Val Gly Val Pro Gly Val Gly Val Pro Gly Val Gly
            660                 665                 670
Val Pro Gly Lys Gly Val Pro Gly Val Gly Val Pro Gly Val Gly Val
            675                 680                 685
Pro Gly Val Gly Val Pro Gly Ala Gly Ala Gly Ser Gly Ala Gly Ala
```

-continued

```
            690                 695                 700
Gly Ser Gly Ala Gly Ala Gly Ser Gly Ala Gly Ala Gly Ser Gly Val
705                 710                 715                 720
Gly Val Pro Gly Val Gly Val Pro Gly Val Gly Val Pro Gly Val Gly
                    725                 730                 735
Val Pro Gly Lys Gly Val Pro Gly Val Gly Val Pro Gly Val Gly Val
                740                 745                 750
Pro Gly Val Gly Val Pro Gly Ala Gly Ala Gly Ser Gly Ala Gly Ala
            755                 760                 765
Gly Ser Gly Ala Gly Ala Gly Ser Gly Ala Gly Ala Gly Ser Gly Val
770                 775                 780
Gly Val Pro Gly Val Gly Val Pro Gly Val Gly Val Pro Gly Val Gly
785                 790                 795                 800
Val Pro Gly Lys Gly Val Pro Gly Val Gly Val Pro Gly Val Gly Val
                805                 810                 815
Pro Gly Val Gly Val Pro Gly Ala Gly Ala Gly Ser Gly Ala Gly Ala
            820                 825                 830
Gly Ser Gly Ala Gly Ala Gly Ser Gly Ala Gly Ala Gly Ser Gly Val
            835                 840                 845
Gly Val Pro Gly Val Gly Val Pro Gly Val Gly Val Pro Gly Val Gly
850                 855                 860
Val Pro Gly Lys Gly Val Pro Gly Val Gly Val Pro Gly Val Gly Val
            870                 875                 880
865
Pro Gly Val Gly Val Pro Gly Ala Gly Ala Gly Ser Gly Ala Gly Ala
                885                 890                 895
Gly Ser Gly Ala Gly Ala Gly Ser Gly Ala Gly Ala Gly Ser Gly Val
            900                 905                 910
Gly Val Pro Gly Val Gly Val Pro Gly Val Gly Val Pro Gly Val Gly
            915                 920                 925
Val Pro Gly Lys Gly Val Pro Gly Val Gly Val Pro Gly Val Gly Val
            930                 935                 940
Pro Gly Val Gly Val Pro Gly Ala Gly Ala Gly Ser Gly Ala Gly Ala
945                 950                 955                 960
Gly Ser Gly Ala Gly Ala Met Asp Pro Gly Arg Tyr Gln Asp Leu Arg
                965                 970                 975
Ser His His His His His
            980
```

REPEAT SEQUENCE PROTEIN POLYMER ACTIVE AGENT CONGJUGATES, METHODS AND USES

RELATED APPLICATION

This application claims priority under 35 U.S.C. §119 of U.S. Provisional Application Ser. No. 60/470,464 filed May 14, 2003. This application is a continuation of U.S. Ser. No. 10/845,936, filed May 14, 2004 now abandoned.

STATEMENT OF JOINT RESEARCH AGREEMENT

This application describes and claims an invention made by parties to a Joint Research Agreement between Genencor International, Inc. and The Dow Corning Corporation.

FIELD OF THE INVENTION

The present invention relates to conjugates formed from repeat sequence protein polymers and various active agents, methods of manufacture, and, more particularly, to applications comprising them.

BACKGROUND OF THE INVENTION

Proteins have been used in wide variety of products to perform a variety of functions and to impart desired characteristics to product formulations. Proteins have also been used to provide films and substrates which confer specifically desirable properties related to function, appearance, texture, and durability to many products in home-care, health-care, and many other consumer and industrial market segments.

However, natural proteins may not exhibit all desired characteristics and functions when used in product formulations. For example, natural silk proteins may impart durability but may also form tight, hard fibers that are not suitable for film formation. Many natural proteins have a low isoelectric point, and the low isoelectric point reduces the affinity of the protein for the negatively charged substrates. This is particularly problematic in personal care formulations where target substrates such as skin and hair typically are negatively charged, and proteins may accumulate on hair or skin over time. Additionally, more than one protein may be needed to impart all desired characteristics to a given formulation, and the necessity of using more than one protein may increase the cost and production time for a given product. Proteins may be chemically modified or quaternized in order to make them more suitable for inclusion in desired applications. However, even chemically modified proteins may not have all desired characteristics.

Active agents such as fragrances, dyes, tints, UV actives, sunscreens, lanolin, vitamins, bleaches, thickening agents, silicones, proteins/peptides, enzymes, antimicrobials and preservatives have been added to various products to impart a number of desired characteristics or functions. For example, specifically in personal care products, silicones have been used to provide protection and moisturization. Amino functional silicones may polymerize in air and provide improved compatibility, electrostatic reduction, and soft touch for hair. Silicones may also provide lubrication and gloss for hair, skin, or nails. Fragrances have been used as finishing ingredients to impart a desired odor. Radioprotective agents have been employed in a variety of products directed to UV-sensitive applications including personal care, clothing and home care products.

Many active agents lose viability over time and may not exhibit good bulking activity or good film forming characteristics. Many active agents may be insoluble in water, and thus the active agents may have to be applied as aqueous emulsions. For instance, proteins and peptides may be desirable active agents, particularly for protein-based applications, but incorporation into formulations may be problematic due to their generally high levels of hydrophobicity, and incorporation into material substrates may subject them to laundering or other cleaning effects, causing loss of the active agent as well as functional efficacy, over time. Thus, the active agents may not be suitable for all applications, and their inclusion in certain applications may be difficult due to their interactive properties such as hydrophobicity, and/or binding and structural limitations.

Thus, there remains a need in the art for preparations that have desired characteristics of proteins and active agents, and for methods of deliberately tailoring the proteins and active agents to the unique product and delivery demands of specific applications. There also remains a need in the art for products incorporating such preparations.

SUMMARY OF THE INVENTION

Accordingly, the present invention meets that need by providing biomolecular recombinant repeat sequence protein polymer active agent conjugates to be used in various product formulations suitable for many specific applications. Repeat sequence protein polymers are engineered proteins which provide a scaffolding to which active agents may be bound. In particular, they enhance the ability to utilize proteins and peptides as active agents. Biomolecular conjugates may be formed between repeat sequence protein polymers and protein/peptide active agents which overcome many of the hydrophobicity, solubility, and binding limitations, and increase their functional applicability. In particular, the biomolecular conjugates of the present invention allow the use of protein/peptide active agents in applications for which a total protein environment is desirable.

For purposes of defining and describing the present invention, "repeat sequence protein polymer" (RSPP) refers to a polymer comprising repeating amino acid sequence units, which repeating units are derived from a natural or synthetic protein. For example, the repeating sequence units may be derived from natural structure supporting materials such as silk, elastin, and collagen. Alternatively, the repeating sequence units may be derived from synthetic structures.

For purposes of defining and describing the present invention, "personal care composition" refers to a product for application to the skin, hair, nails, oral cavity and related membranes for the purposes of improving, cleaning, beautifying, therapeutically treating, caring for these surfaces and membranes.

For purposes of defining and describing the present invention, "an effective amount" refers to the amount of repeat sequence protein polymer which is added to a personal care composition to provide the composition with a desired characteristic or characteristics.

For purposes of defining and describing the technology, the term "dispersed phase" is a term well-known to one skilled in the art of emulsion technology, which means that the phase exists as small particles or droplets that are suspended in and surrounded by a continuous phase. The dispersed phase is also known as the internal or discontinuous phase.

For purposes of defining and describing the present invention "active agent" shall be understood as referring to a suitable product component including, but not limited to, silicones, fragrances, dyes, tints, UV actives, sunscreens, lanolin, vitamins, bleaches, thickening agents, proteins, peptides, enzymes, antimicrobials and preservatives.

For purposes of defining and describing the present invention, the term "protein" as used herein, shall be understood as comprising greater than fifty (50) amino acids, while the term "peptide" as used herein, shall be understood as comprising 50 or less amino acids.

In accordance with one embodiment of this invention, the biomolecular conjugates comprise the conjugation product of a repeat sequence protein polymer and at least one active agent. Specific embodiments are directed to such biomolecular conjugates wherein the repeat sequence protein polymer is a silk elastin like polymer (SELP), and more specifically where it comprises SELP47K. Other specific embodiments are directed to biomolecular conjugates wherein at least one of the active agents is a silicone, fragrance, dye, tint, UV active, lanolin, vitamin, bleach, thickening agent, protein, peptide, enzyme, preservative, and in some embodiments the conjugation is formed from more than one active agent.

An additional aspect of the invention relates to the repeat sequence protein polymer active agent conjugates formulated into personal care product compositions, and to processes for making personal care product compositions utilizing the biomolecular conjugates. In accordance with another aspect of the present invention, the personal care product formulation is a skin protection cream. Further embodiments relate to emulsions and surfactant systems comprising the biomolecular conjugates useful in a variety of applications.

Another more specific embodiment of the invention relates to biological conjugates comprising SELP and at least one active agent comprising a protein or peptide wherein the SELP and the protein conjugate as a fusion protein. Very specific aspects of this embodiment include fusion protein conjugates formed from active agents including antimicrobial peptides, green fluorescent protein, radioprotective P4 peptides, and/or cotton binding peptides. In one embodiment, more than one protein or peptide active agent is conjugated with the SELP.

An additional embodiment relates to methods of producing biomolecular conjugates comprising fusion protein conjugates comprising a conjugation product of a repeat sequence protein polymer and at least one active agent comprising a protein or peptide. This method embodiment comprises selecting the repeat sequence protein polymer and the protein active suitable for a desired application, obtaining a gene encoding the repeat sequence protein polymer and a gene encoding the at least one active agent comprising a protein or peptide, constructing a conjugate gene from the gene encoding the repeat sequence protein polymer and the gene encoding the at least one active agent, expressing the conjugate gene to form an expression product comprising the fusion protein conjugate, fermenting the expression product comprising the fusion protein conjugate, and purifying the fusion protein conjugate. Further specific embodiments are directed to methods which employ specific proteins as the active agents, and/or more than one protein or peptide active agent.

A further embodiment of the invention is directed to methods for providing biomaterial adapted for at least one predetermined desirable function comprising selecting a biomolecular conjugate comprising a conjugation product of a repeat sequence protein polymer and at least one active agent, wherein the repeat sequence protein polymer comprises a silk elastin polymer and the at least one active agent comprises a protein or peptide, and further wherein the conjugation product comprises a fusion protein, according to the predetermined desirable function; and incorporating the biomolecular conjugate into a material. In another aspect, a biomaterial adapted for at least one predetermined desirable function is provided. Very specific embodiments provide applications for particular biomolecular conjugates.

Accordingly, it is a feature of the present invention to provide repeat protein polymer active agent conjugates, methods of their production, and product compositions and materials incorporating them in order to deliver a number of benefits.

DETAILED DESCRIPTION OF THE PREFERRED EMBODIMENTS

The present invention utilizes recombinant repeat sequence protein polymers containing repeating units conjugated with at least one active agent to serve as components in a variety of personal care, health care, home care, and other consumer products. The repeating units of the repeat sequence protein polymers may be of natural structure supporting materials such as silk, elastin, and collagen, or the repeating units may be of synthetic structure. Typically, the present invention involves synthesizing the repeat sequence protein polymers, forming the repeat sequence protein polymer active agent biomolecular conjugates, and adding the repeat sequence protein polymer active agent conjugates to the product formulations, or directly to materials for which a specific function or characteristic conferred by the biomolecular conjugates is desired.

The recombinant repeat sequence protein polymers of the present invention are comprised of naturally or non-naturally occurring repeating units. There are more than six hundred repeat protein sequences known to exist in biological systems as of the filing of this application. For example, well known proteins containing repeat protein sequences include abductin, elastin, byssus, flagelliform silk, dragline silk, gluten high molecular weight (HMW) subunit, titin, fibronectin, leminin, and collagen. Additionally, synthetic repeating units may be utilized. Individual repeating units will generally comprise from 3 to 50 amino acids, and will usually have the same amino acid appearing at least twice in the same unit. Typically, individual units will comprise from about 3 to 35 amino acids. Therefore, each individual unit will typically be formed from about 3 to 35 amino acids. Different unit combinations may be joined together to form a block polymer or alternating block polymer. Typically, the polymers will have the following formula:

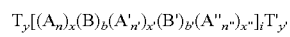

wherein:

T is an amino acid sequence of from about 1 to 100 amino acids, usually 1 to 60 amino acids, which may be any sequence, generally being fewer than 20% of the total number of amino acids in the repeat protein polymer;

y is 0 or 1;

T' and y' are the same as or different from T and y respectively, wherein the analogous symbols have the same definition as their counterparts;

A is an individual unit of a repeat amino acid sequence;

n is an integer of at least 2 and not more than 250;

x is 0 or an integer of at least 1 and will vary with the number of different amino acids in A so as to provide for at least 30 amino acids in each A repeat sequence;

A', n', and x' are the same as or different from A, n, and x respectively, at least one being different, wherein the analogous symbols have the same definition as their counterparts;

A", n", and x" are the same as or different from A, n, and x respectively, at least one being different, wherein the analogous symbols have the same definition as their counterparts;

B is any amino acid sequence of 4 to 50 amino acids, usually being a functional sequence that results in a biological or chemical function or activity;

b is 0 to 3;

B' and b' are the same as or different from B and b respectively, wherein the analogous symbols have the same definition as their counterparts; and i is 1 to 100, usually 1 to 50, more usually 1 to 35.

Additionally, the protein polymer may have amino acid sequences that link the repeating A, A', and A" units or amino acid sequences that link between the individual A, A' or A" units. These linking sequences are typically from 1 to 10 amino acids and serve to link the repeating units. These repeat polymers can be synthesized by generally recognized methods of chemical synthesis (for example, L. Andersson et al., *Large-scale synthesis of peptides*, Biopolymers 55(3), 227-50 (2000)), genetic manipulation (for example, J. Cappello, Genetically Engineered Protein Polymers, Handbook of Biodegradable Polymers, Domb, A. J.; Kost, J.; Wiseman, D. (Eds.), Harvard Academic Publishers, Amsterdam; pages 387-414), and enzymatic synthesis (for example, C. H. Wong & K. T. Wang, *New Developments in Enzymatic Peptide Synthesis*, Experientia 47(11-12), 1123-9 (1991)). For example, the repeat sequence protein polymers of the present invention may be synthesized using the methods described in U.S. Pat. Nos. 5,243,038 and 6,355,776, the disclosures of which are incorporated by reference herein. In another example, the repeat sequence protein polymers can by synthesized utilizing non-ribosomal peptide synthase (for example, H. V. Dohren, et al., Multifunctional Peptide Synthase, Chem. Rev 97, 2675-2705(1997).

Individual repeat amino acid sequence units of particular interest include units found in silk-, elastin-, collagen-, abductin-, byssus-, gluten-, titin-, extensin-, and fibronectin-like proteins. Silk-like proteins have a repeating unit of SGAGAG (G=glycine; A=alanine; S=serine) (SEQ ID NO. 1). This repeating unit is found in naturally occurring silk fibroin protein, which can be represented as GAGAG (SGAGAG)$_8$SGAAGY (Y=tyrosine) (SEQ ID NO. 2). Elastin-like proteins have a base repeating unit of GVGVP (V=valine; P=proline) (SEQ ID NO.3). This repeating unit may be found in naturally occurring elastin. Collagen-like proteins have repeating units of G-x-y (x=any amino acid, often alanine or proline; y-any amino acid, often proline or hydroxy-proline). Abductin-like proteins have a base repeating unit of GGFGGMGGGx (F=phenylalanine; M=methionine, x=any amino acid) (SEQ ID NO. 4). Byssus-like proteins have a repeating unit of (GPGGG) (SEQ ID NO. 5). Gluten-like proteins of the high molecular weight subunit have repeating units of PGQGQQ (SEQ ID NO. 6), GYYPTSPQQ (SEQ ID NO. 7), and GQQ (Q=glutamine; Y=tyrosine; T=threonine) SEQ ID NO. 8). Titin-like proteins have a repeating units of PPAKVPEVP-KKPVPEEKVPVPVPKKPEA (K=Lysine, E=Glutamic Acid) (SEQ ID NO. 9) and are found in the heart, psoas, and soleus muscle. Extensin-like proteins have repeating units of SPPPPSPKYVYK (SEQ ID NO. 10). Fibronectin-like proteins have repeating units of RGDS (R=arginine; D=aspartic acid) (SEQ ID NO. 11).

Additional repeating units of interest are found in gliadin, glue polypolypeptide, ice nucleating protein, keratin, mucin, RNA polymerase II, and resilin. Gliadin has a repeating unit of PQQPY (SEQ ID NO. 12). The glue polypeptide has a repeating unit of PTTTK (SEQ ID NO. 13). The ice nucleating protein has a repeating unit of AGYGSTGT (SEQ ID NO. 14). Keratin has repeating units of YGGSSGGG (SEQ ID NO. 15) or FGGGS (SEQ ID NO. 16). Mucin has a repeating unit of TTTPDV (Seq. ID No. 17). RNA polymerase II has a repeating unit of YSPTSPS (SEQ ID NO. 18). Additionally, resilin, a rubber-like protein contains repeating units.

It will be understood by those having skill in the art that the repeat sequence protein polymers of the present invention may be engineered to include appropriate repeating units in order to provide desired characteristics. For example, the repeat sequence protein polymers may be produced to have moisturizing properties, to have a high glass transition temperature for hardness or strength, to have a high cloud temperature for heat sensitive applications, or to enhance delivery of particular active agents into materials. Similarly, the proteins may be produced to have a high isoelectric point to increase the affinity of the protein to certain substrates. The molecular weight of the protein may be chosen in order to increase or decrease water solubility as desired.

Repeat sequence protein polymers utilizing the natural or synthetic repeating units may have their properties altered by appropriate choice of different units, the number of units in each multimer, the spacing between units, and the number of repeats of the multimer combination assembly. Multimer refers to the portion of the polymer represented by $T_y[(A_n)_x (B)_b(A'_{n'})_{x'}(B')_{b'}(A''_{n''})_{x''}]_i T_{y'}$ in the above formula. The spacing between units refers to the other amino acid sequences represented by B or B' in the above formula. Preferred polymers are combinations of silk units and elastin units to provide silk-elastin polymers having properties distinctive from polymers having only the same monomeric unit.

It will be understood by those having skill in the art that the repeat sequence protein polymers of the present invention may be produced to have a combination of desirable characteristics. For example a polymer having silk repeating units and elastin repeating units may be produced to impart durability due to the silk repeating units and to impart flexibility due to the elastin repeating units. Additionally, the silk-elastin polymer may exhibit other desirable properties such as good clear film and hydrogel formation, which the individual monomeric units may not exhibit. The silk-elastin polymer may be hydrophilic and water soluble. The silk-elastin polymer may also exhibit a high cloud temperature which is desirable in heat sensitive applications. The silk-elastin polymer may have a high isoelectric point which may make the polymer more substantive to skin and hair. The silk-elastin polymer may further exhibit self assembly into fibers and films which may be desirable in some applications.

It will be further understood by those having skill in the art that the repeat sequence protein polymers of the present invention may be monodispersed or polydispersed. For purposes of defining and describing the present invention, "monodispersed" polymers are polymers having a single defined molecular weight. For purposes of defining and describing the present invention, "polydispersed" polymers are polymers that have been subjected to proteolysis and have a distribution of molecular weights.

Once a suitable repeat protein has been synthesized and purified, it may be conjugated with a suitable active agent or agents to form the repeat sequence protein polymer active agent biomolecular conjugates. For purposes of defining and describing the present invention, "repeat sequence protein polymer active agent biomolecular conjugate" will be understood as referring to compounds having at least one repeat sequence protein polymer portion covalently bonded to at least one active agent portion. For purposes of defining and describing the present invention "active agent" shall be understood as referring to a suitable product component including, but not limited to, silicones, fragrances, dyes, tints, UV actives, sunscreens, lanolin, vitamins, bleaches, thickening agents, proteins, peptides, enzymes, antimicrobials and preservatives. The biomolecular conjugates of the present invention may be formed in any suitable manner, and the conjugates may be of any conjugate form. For example, the conjugates may be block polymers.

Any suitable silicone may be used to form the biomolecular conjugates of the present invention. Suitable silicones include silicones containing an epoxy functional group. Such epoxy functional silicones may be used to form a repeat sequence protein polymer silicone conjugate by linking the epoxy functional group to an amine containing group such as a lysine on a suitable repeat sequence protein polymer. Other suitable silicones include Polydimethyl siloxanes such as (3-glycidoxypropyl) diethoxy-methylsilane and 3-chloropropylmethyldimethoxysilane that may be used to form the conjugates of the present invention. Additionally, silicone resins, such as trimethyl siloxy silicate and PEG (PEG/PPG-20/15 and PEG-12 from G.E. Silicones, Waterford, New York), may be used to form biomolecular conjugates for use in makeup and skin care formulations.

Silicone surfactants, such as dimethicone copolyol, cetyl dimethicone polyol, and capryl dimethicone ethoxyglucoside, may be used to form conjugates for use in skin and sun care formulations. Alkyl modified silicones, such as steryl methicone, lauryl methicone, and stearoxy dimethicone, may be suitable for conjugates for use in skin care product formulations. Gum fluid blends, phenyl fluids, and dimethyl fluids may be suitable for conjugates that may be incorporated in hair care formulations. Quaternized ammonium salts of suitable silicones may be used to form conjugates that may provide enhanced conditioning properties to hair and skin care product formulations. For example, glycidyltrimethylammonium chloride may be used to form the biomolecular conjugates of the present invention. The silicones may contain one or more amino functional groups in order to provide enhanced bulking. For example, the silicones may be aminodimethicone or trimethylsiloxyamodimethicone.

Any suitable fragrance molecule may be used to form the biomolecular conjugates of the present invention. For example, allyl cinnamic acid may be used to form the conjugates of the present invention. Other fragrance molecules include, but are not limited to adipic acid, phenyl acetic acid, citronellyl valeric acid, and vanillic acid. Any suitable vitamin may be used to form the conjugates of the present invention. For example, vitamin C may be used. Additionally, other vitamins such as B, D, K, and their derivatives may be used.

Any suitable UV or radioprotective active may be used to form the biomolecular conjugates of the present invention. For example, p-hydroxy cinnamic acid may be used as the active agent. Additionally, other UV actives such as phenylbenzimidazole sulfonic acid, octyl methoxycinnamate, benzophenone-3, titanium dioxide, and octyl salicylate, butylmethoxydibenzoymethane, amyl methoxy cinnamate, and menthyl anthranilate, and their derivatives may be used. Naturally-derived peptide-based UV agents (see, e.g., K. H. Dittmann, N. Gueven, C. Mayer, and H-P. Rodemann, *Protein Engineering*, 14, 2001, 157-160) biomolecular conjugates may be used in applications to render a variety of surfaces protective of uv radiation when desirable. Non-limiting examples include textiles, wound dressings, skin creams, and coatings to be applied to UV-sensitive surfaces. A specific conjugate with particular utility in UV-sensitive applications is P4-SELP47K.

Any suitable dye may be used to form the conjugates of the present invention. For example, Fluorescein 5(6) isothiocyanate (FITC) may be used. Any suitable preservative may be used to form the conjugates of the present invention. For example, methyl and propyl paraben, imidazilidinyl urea, and sorbic acid may be used as the active agent of the present invention. Any suitable enzyme may be used to form the conjugates of the present invention. For example, hydrolases, proteases, lipases, oxidases, peroxidases, amylases, carbohydrolases, superoxide dismutases, and Q10 or PQQ coenzyme may be used.

Many proteins and peptides capable of forming fusion proteins with repeat sequence protein polymers may be used to form the biomolecular conjugates of the present invention. Such proteins include, but are not limited to, antimicrobial peptides (AMPs), cotton binding peptides (CBPs), peptide-based UV protective agents, and green fluorescence protein (GFPs). Persons of ordinary skill in the art will immediately recognize that any protein or peptide comprising a desirable functionality or conferring a desirable characteristic to a substrate in which it is incorporated, which is capable of being fused with a repeat sequence protein polymer, may be used to form the biomolecular conjugates of the present invention.

The biomolecular conjugates of the present invention may be formed in any suitable manner. Generally, a chemical or biochemical method will be selected to form the conjugate based upon what functional groups are available for making conjugated materials of repeat sequence protein polymers and active agents. For example, thermal reaction, chemically assisted conjugations, such as conjugations utilizing glutaraldehyde, diisocyanates, carbodimide, living radical polymerization, and enzymatically assisted conjugations, such as conjugations utilizing lipase and transglutaminase, may be used to form the conjugates of the present invention. Generally, the active agent may have functional groups including, but not limited to, epoxy, chloroalkyl, amino, carboxy, sulfhydryl, vinylsulfones, and the like. The methods outlined in *Bioconjugation*, Eds., Aslam & Dent, Macmillan Publications, London, 1998, Chapter 6 may be used to form the conjugates of the present invention.

The biomolecular conjugates formed from the fusion of repeat sequence protein polymers and protein, peptide or enzyme actives may be formed via biological production methods well-known in the art, for example, DNA synthesis, polymerase chain reaction, recombinant DNA technologies, microbial fermentation, and advanced protein recovery techniques. These techniques allow production of specifically designed, sequence-controlled repeat sequence protein polymer—protein/peptide/enzyme conjugates that may be incorporated as components of biomaterials so that the biomaterials exhibit predetermined physical, functional and biological properties.

The repeat sequence protein polymer active agent conjugates of the present invention may be added to any suitable personal care product formulation. For example, the conjugates may be added to hair rinse formulations. The conjugates may be used in shampoos, gels, mousses, and other hair care products. The conjugates may be suitable for use in skin care products such as moisturizers, toners, and makeup. The conjugates may also be suitable for use in nail products such as polishes and polish remover.

The biomolecular conjugates may be present in any suitable amount in product formulations. For example, the repeat sequence protein polymer active agent conjugates may comprise from about 0.001% to about 10% by weight of the composition. More generally, the repeat proteins may comprise about 0.01% to about 5% by weight of the composition, more preferably about 0.01% to about 1% by weight of the composition.

In accordance with one embodiment of the present invention, the repeat sequence protein polymer active agent conjugates may be formulated into a variety of emulsions. The emulsions may provide moisturizing, softening, film formation, feel improvement, optical effects, strengthening, firming, and conditioning properties. The emulsions may contain:

| Water | qs |
|---|---|
| Emulsifier(s) | 1-5% |
| Thickener(s)/Stabilizer(s) | 0.1-3% |
| Emollient(s) | 2-10% |
| Opacifier(s) | 0-10% |
| Humectant(s) | 0-10% |
| Repeat sequence protein polymer active agent conjugate(s) | 0.001-10% |
| Functional ingredient(s) | 0.001-25% |
| Preservative | qs |
| Finishing ingredient(s) | qs |

It will be understood that the emulsions may additionally contain other suitable components.

Suitable emulsifiers may be anionic, cationic, or nonionic in nature. For example, suitable emulsifiers include, but are not limited to, TEA stearate, ethoxylated fatty acids, or alcohols. Suitable thickeners may be any combination of ingredients used to modify product viscosity or rheology. The thickeners may be natural, and natural thickeners may include silicas, magnesium aluminum silicate, xanthan gum, and alginates. The thickeners may alternatively be polymeric, and polymeric thickeners may include acrylate crosspolymers, polyacrylic acid, and modified cellulosics. The thickeners may also include crystalline agents such as fatty acids and alcohols, and suitable crystalline agents include stearyl alcohol or stearic acid.

The emollients may be any combination of one or more ingredients used to modify product feel and aesthetics. Suitable emollients include: simple and complex esters such as isopropyl myristate and octyldodecyl stearoyl stearate; triglycerides such as capric/caprylic triglyceride; waxes such as carnauba and shea butter; vegetable or animal oils such as castor, coconut, and rice bran oil; fatty alcohols such as stearyl, myristyl, cetyl and behenyl alcohol; and fatty acids such as stearic, lauric and oleic acid.

Opacifiers may be any combination of one or more ingredients used to modify product appearance. Suitable opacifiers include, but are not limited to, fatty alcohols such as stearyl, myristyl, cetyl and behenyl alcohol and fatty acids such as stearic, lauric and oleic acid). Suitable humectants may be any combination of one or more ingredients used to retain moisture in the formula and impart hydration to the user. Suitable humectants include, but are not limited to, glycerin, propylene glycol, and sorbitol.

Functional ingredients may be any combination of one or more ingredients added to impart a specific effect when used. These can include: UV absorbers such as octyl methoxycinnamate, benzophenone-3, titanium dioxide, and octyl salicylate; film-forming agents such as VP/Eicosene polymer; cosmeceutical agents such as peptides and proteins, alpha hydroxy acids, and retinol and retinoic acid derivatives; antioxidants such as tocopherol and derivatives thereof and ascorbic acid and derivatives thereof; vitamins such as B, D, K and their derivatives; antiperspirant actives such as aluminum hydroxide and zirconium hydroxide; depilating agents such as thioglycolate salts; anti-acne agents such as salicylic acid and benzoyl peroxide; abrasives and exfoliants such as silicates, pumice, and polyethylene; and extracts of plant, fruit, vegetable or marine sources.

Suitable preservatives may be any combination of ingredients approved by regulatory agencies and acceptable for use in cosmetic applications. For example, methyl and propyl paraben, imidazolidinyl urea, and sorbic acid may be used as perservatives. Finishing ingredients may be any combination of one or more ingredients added to adjust a formula's characteristics. Finishing ingredients may include: fragrance; colors; chelating agents such as tetrasodium EDTA; and pH buffers such as citric and phosphoric acid and salts.

Those skilled in the art may modify the illustrative emulsion formula for a variety of personal care applications. The emulsion formula may be used to form creams, lotions, moisturizers, facial cleansers, depilatories, masks, suncare products, antiperspirants, acne products, foundations, hair conditioners, hair relaxers, hair treatments, mascara, nail products, lip products, shaving products, and toothpaste, and the like. It will be understood that, if an active agent is conjugated with a repeat sequence protein polymer, the active agent will not generally be included separately in the emulsion formulation. However, some active agents, such as silicones, may be included in conjugated and unconjugated form in the formulations as needed.

In accordance with another embodiment of the present invention, repeat sequence protein polymer active agent biomolecular conjugates may be formulated into a variety of surfactant systems. The surfactant systems may provide a number of properties to personal care products including moisturizing, softening, film formation, feel improvement, optical effects, strengthening, firming and conditioning. Typical surfactant systems may contain, but is not limited to, the following components:

| Water | qs |
|---|---|
| Primary surfactant(s) | 0.1-15% |
| Secondary surfactant(s) | 0.1-10% |
| Rheology modifier(s) | 0.1-5% |
| Alcohol(s) | 0-25% |
| Functional ingredient(s) | 0-10% |
| Conditioning ingredient(s) | 0-5% |
| Preservative(s) | qs |
| Finishing ingredient(s) | qs |
| Repeat sequence protein polymer active agent conjugate(s) | 0.001-10% |

It will be understood that additional, suitable components may be included in the surfactant systems.

Primary surfactants may be any combination of one or more ingredients used to reduce surface tension or create foam. Surfactants may include; anionic surfactants such as alkyl sulfates, ether sulfates, alpha olefin sulfonates, and soap; amphoteric surfactants such as glucosides, glutamates, carboxylates, isethionates, carboxylates, glycinates, and lauramphoacetates; zwitterionic surfactants such as betaines and sultanes; or nonionic surfactants such as fatty alcohol ethoxylates, fatty acid ethoxylates, and amine oxides Secondary surfactants may be any combination of one or more ingredients used to modify foam characteristics and quality, stabilize foam, or reduce irritation. These can include, for example, cocoamidopropyl betaine, monoethanolamides, and diethanolamides. Suitable rheology modifiers can be any combination of one or more ingredients used to modify product appearance, viscosity or rheology. Rheology modifiers may be natural rheology modifiers, including salt, silicas, magnesium aluminum silicate, xanthan gum, guar derivatives, and alginates. Rheology modifiers may be polymeric rheology modifiers including acrylate crosspolymers, modified cellulosics, and polyacrylic acids. They may also include opacifiers and crystalline agents such as fatty acids and alcohols including stearyl alcohol or stearic acid. Suitable alcohols may be any combination of one or more ingredients added to provide astringency, cooling, volatility, or solubilization. For example, suitable alcohols include ethanol and isopropanol.

Functional ingredients may be any combination of one or more ingredients added to impart a specific effect when used. These can include: UV absorbers such as octyl methoxycinnamate and benzophenone-3; styling and film-forming agents such as polyvinyl pyrolidone (PVP) and PVP/polyvinyl alchol (PVA) polymers; cosmeceutical agents such as peptides, proteins, alpha hydroxy acids, retinal, and retinoic acid derivatives; antioxidants such as tocopherol and derivatives thereof and ascorbic acid and derivatives thereof; vitamins such as vitamins B, D, K and their derivatives; anti-acne agents such as salicylic acid and benzoyl peroxide; anti-dandruff agents such as zinc pyrithione and selenium sulfide; and conditioning agents such as cationic agents and extracts of plant, fruit, vegetable or marine sources.

Conditioning agents may be any combination of one or more ingredients added to impart moisturization, feel, smoothing, anti-static effects or shine. Suitable conditioning agents may include: cationic polymers such as polyquaternium-10 and polyquaternium-11; quaternized fatty acids such as cetyl trimethyl ammonium chloride; animal or vegetable proteins and their derivatives such as hydrolyzed wheat protein and hydrolyzed collagen; silicone derivatives such as dimethicones, amodimethicones, phenyl trimethicones, and volatile silicones; emollient oils such as isopropyl myristate and capric/caprylic triglyceride; and humectants such as glycerin and propylene glycol.

Those having skill in the art can modify this illustrative surfactant system formula for a variety of personal care applications. For example, the surfactant formula may be modified to form shampoos, body cleansers, facial cleansers, hair conditioners, hair gels, hair treatments, facial toners, fragrance products, and mouthwashes, and the like. It will be understood that, if an active agent is conjugated with a repeat sequence protein polymer, the active agent will not generally be included separately in the surfactant formulation. However, some active agents, such as silicones, may be included in conjugated and unconjugated form in the formulations as needed.

The repeat sequence protein polymer active agent biomolecular conjugates of the present invention may be engineered to provide many desirable properties to personal care products. For example, the conjugates may provide improved sensation to touch of the skin and hair, lubrication to wet or dry hair, improved longevity, and better film formation and cross-linking. The repeat sequence protein polymer component may be able to provide improved substantivity to the hair, skin, and nails without causing a decrease in moisturization. The conjugates may additionally allow an active agent such as silicone to be incorporated into personal care formulations without the use of surfactants. Additionally, the conjugates of the present invention may not cause an appreciable level of protein accumulation to hair because they could be removed by shampooing.

It will be understood by those having skill in the art that the repeat sequence protein polymer portion and the active agent portion of the conjugates of the present invention may be chosen to provide desired properties. For example, the repeat sequence protein polymer may be chosen to have a high isoelectric point to increase affinity to the hair and skin while the active agent is chosen to provide moisturization. It will be further understood that the repeat sequence protein polymer and/or the active agent portion of the conjugate may be chosen to impart one or more desirable properties to the conjugate.

In accordance with another embodiment of the invention, the active agents comprise proteins, peptides or enzymes capable of forming biomolecular conjugates with the repeat sequence protein polymers via protein fusion methods. For purposes of defining the invention, "fusion protein" as used herein is understood to mean the product of combining two independent, proteins/peptides by a coupling involving a chemical bond. Fusion proteins may be created using chemical, enzymatic, physical, or genetically engineered means. A specific repeat sequence protein polymer particularly useful in the formation of these conjugates is SELP47K (SEQ. ID. NO.19). Examples of particular conjugate embodiments include those comprised of SELP47K conjugates with anti-microbial peptides (AMPs), Green fluorescent proteins (GFPs), Cotton Binding Peptides (CBPs) and radioprotective P4. These engineered biopolymers closely simulate natural polymers but provide additional desirable functions. One aspect relates to methods for providing the repeat sequence protein polymers that incorporate the protein or peptide actives, and other aspects, detailed in the examples below provide processes employing biological production methods well-known in the art, such as DNA synthesis, polymerase chain reaction, recombinant DNA technologies, microbial fermentation and advance protein recovery techniques, which provide specifically designed, sequence-controlled repeat sequence protein polymers with predetermined properties. A further aspect is directed to biomaterials and applications incorporating these conjugates.

A specific embodiment of the invention relates to novel bioengineered biomaterials that incorporate AMP agents. Antimicrobial peptides (AMPs) are the first nonspecific defense system of all organisms against microbial infection, including humans and plants. These ribosomally-synthesized peptides are powerful protectants against microbes. Their most remarkable property is that development of microbial resistance against them is uncommon. For this reason, using AMPs in creating antimicrobial materials offers long-term efficacy and stability against microbial infection. Non-limiting examples of such applications include incorporation into textiles, including UV-protective textiles; filters, including air filters and surgical masks; protective garments, including surgical gowns, and garments designed for biological warfare defense; wound dressings; skin cream; and coatings intended to provide a hygiene concerned surface which would protect against, e.g., micro-organisms, spores and viruses.

Another specific embodiment provides conjugates formed from repeat sequence protein polymers and green fluorescence protein (GFP). A more specific embodiment provides SELP47K-GFP conjugates. These conjugates offer a potential to extend the utility of GFP as a research tool, as, for example, a real time reporter of gene expression. In addition, the conjugates comprising a GFP component, through conferring fluorescent properties when exposed to particular wavelengths of light to biomaterials comprising them, may provide a means of searching and/or identifying. For example, Alzheimer's patients or children prone to wander may wear garments comprising these conjugates, or military personnel may wear such garments enabling military surveillors to distinguish friend from foe. The GFP gene can be obtained from Clonetech, Inc. The repeat sequence protein polymer-GFP conjugate is constructed according to the examples provided below.

A further specific protein-fusion biomolecular conjugate embodiment provides conjugates formed from repeat sequence protein polymers and cotton binding peptide (CBP). Incorporation of CBPs into, for example, fabrics and textiles or cotton gauze dressing, renders these materials more accessible to desirable biomaterials. Other applications relate to fabric care and use of the biomaterials comprising the conjugates to provide detergent formulations suitable for improved cleaning of cotton based clothing. The CBPs employed in the present invention were derived from screening a library of peptides under typical laundry wash conditions. The repeat sequence protein polymer—CBP conjugate offers advantages over the use of cellulose binding modules (CBMs), known in the industry as useful for targeting molecules to cotton substrates. The CPBs, unlike the CBMs, can be made application specific. For example, the CPB can be tailored to meet the application requirements for pH, conductivity, presence of detergent, solvents, etc. Use of CBMs, on the other hand, is limited to those applications where the reaction conditions are the same as the CBM's requirements for binding. A very specific repeat sequence protein polymer utilized to form this conjugate is SELP47K, and the CPB used to form the conjugate with the SELP47K is one that binds to cotton under European detergent standards. Therefore, the SELP47K-CPB conjugate can be used to attach a wider variety and greater amounts of agents to cotton materials as they are sustained through a wash cycle. CBMs do not bind under wash conditions and therefore have limited utility in laundry applications.

Another specific aspect of the invention provides a radioprotective P4-repeat sequence protein polymer conjugate, with a very specific embodiment comprising SELP47K-P4. A further aspect provides biomaterials that incorporate these naturally-derived peptide-based UV agents (see, e.g. K. H. Dittmann, N. Gueven, C. Mayer, and H. P. Rodemann, *Protein Engineering*, 14, 2001, 157-160). Such conjugates may be used in applications to render surfaces protective from UV radiation when desirable. Several non-limiting examples include incorporation into textiles, wound dressings, skin creams, and coatings to be applied to various UV sensitive surfaces. These engineered biopolymers closely simulate natural polymers, but, as conjugates, are also capable of protecting the surfaces from exposure to UV radiation, thereby preventing loss of material value.

A further aspect provides conjugates coupled together by design and/or simple mixing. For example, AMP-repeat sequence protein polymer conjugates, P4-repeat sequence protein polymer conjugates, CBP-repeat sequence protein polymer conjugates, and GFP-repeat sequence protein polymer conjugates, as described above and detailed in the examples below, can be coupled together both by de novo design and/or simple mixing to create multifunctional biomaterials desirable for various applications in home-care, personal care, biodefense, health care, and other consumer and industrial market segments.

In a specific coupled conjugate embodiment, antimicrobial/UV resistant skin binding protein is constructed using P4-SELP47k protein as the backbone protein for the addition of AMP hexamers using the methods disclosed in the examples below for the addition of cecropinA-melettin and/or MBI-28 hexamers to N-terminal and/or C-terminal regions of unmodified SELP47K. A further specific embodiment comprises antimicrobial/cotton binding protein wherein a CottonS2E1-SELP47K protein is used as the backbone protein for the addition of AMP hexamers, while another specific embodiment comprises antimicrobial/cotton binding protein wherein the AMP hexamer is added to the C-terminal or N-terminal region of unmodified SELP47K while the cotton binding hexamer is added to the opposite end of the resulting AMP-SELP47K conjugate using the methods disclosed in the examples illustrating the addition of cotton binding hexamer to unmodified SELP47K. Another coupled embodiment comprises cotton binding/UV resistant skin binding protein wherein the P4-SELP47K protein is used as the backbone protein for the addition of cotton binding hexamer to N-terminal and/or C-terminal regions. An additional coupled conjugate embodiment comprises cotton binding/Antimicrobial/UV resistant skin binding protein wherein P4-SELP47K protein is used as the backbone protein for the addition of cotton binding hexamer to N-terminal or C-terminal regions using the methods disclosed for the addition of cotton binding hexamer to unmodified SELP47K. AMP hexamer is added to the opposite end of the resulting Cotton-P4-SELP47K conjugate using the methods disclosed in prior examples for the addition of AMP hexamer to unmodified SELP47K.

In order that the invention may be more readily understood, reference is made to the following examples, which are intended to be illustrative of the invention, but are not intended to be limiting in scope.

EXAMPLES

Example 1

A genetically engineered silk-elastin polymer (SELP47K) was isolated and purified from *E. coli* bacteria. The *E. coli* containing the SELP47K recombinant DNA was obtained from Protein Polymer Technologies, Inc. of San Diego, Calif. The *E. Coli* may be prepared in accordance with the methods described in U.S. Pat. Nos. 5,243,038 and 6,355,776. The silk-elastin polymer SELP47K had a general structure of:

head-$[(GAGAGS)_2(GVGVP)_3GKGVP(GVGP)_4(GAGAGS)_2]_{13}$-tail (SEQ ID NO. 19).

The polymer contained 886 amino acids, with 780 amino acids in the repeating unit.

Monodispersed silk-elastin protein polymer SEPL47K was produced for application testing in the following manner. *E. coli* fermentation was performed to produce a cell-paste containing monodispersed SELP47K. The cell-paste was placed in ice cold water and homogenized to make the cell extract. The cell-extract was mixed with polyethyleneimine and a filter-aid and was allowed to stir at 7° C. for one hour. The polyetheyleneimine caused precipitation of cell debris and a significant amount of *E. coli* proteins. This SELP47K containing reaction mixture was then filtered using RVDF. The filtered SELP47K solution was then mixed with ammonium sulfate to 25% saturation. This led to precipitation of SELP47K. Precipitated SELP47K and mother liquor was mixed with a filter-aid and again filtered using RVDF. The RVDF cake containing SELP47K and filteraid was mixed with cold water to dissolve the SELP47K. This precipitation and solubilization step was repeated to improve the purity profile of the SELP47K. Purified monodispersed SELP47K was then water-exchanged until the conductivity of SELP solution reached 50 µS/cm². The monodispersed SELP solution was then concentrated to 10% wt/vol and then lyophilized to make powdered monodispersed SELP47K protein polymer. The material was stored at −70° C. until needed for application testing.

Example 2

The purification and preparation of the polydispersed silk-elastin protein polymer for application testing was carried out in the following steps. A cell separation from the fermentation broth was done using microfiltration. A cell disruption to make a cell-extract was done using a French-press. The cell extract was separated from the cell-debris using polyethyleneimine and a filter-aid. The cell-extract was mixed with ammonium sulfate to 25% saturation to precipitate the silk-elastin protein polymer. The precipitated silk-elastin protein polymer was further purified by dissolving it in water and precipitating it with ammonium sulfate.

In order to prepare a polydispersed silk-elastin protein polymer, the precipitated silk-elastin protein polymer was again dissolved in water and mixed with a trace amount of commercial protease. The commercial protease was then inactivated and destroyed by acid treatment. The polydispersed silk-elastin protein polymer was then ultrafiltered until the silk-elastin protein polymer solution reached an electrical conductivity of 50 $\mu S/m^2$.

The polydispersed silk-elastin protein polymer solution was concentrated to 10 wt % and was lyophilized. The lyophilized polydisperesed silk-elastin protein polymer powder was stored at −70° C. until use.

Example 3

A SELP47K-EpoxySilane conjugate was prepared in the following manner. A 1-10% solution of SELP47K, in accordance with Example 1, was prepared in 100 mM bicarbonate buffer pH 9.7. The solution was stirred to dissolve all the protein polymer. The protein polymer solution was then mixed with (3-glycidoxypropyl)diethoxy-methylsilane or with 3-glycidoxypropyl)dimethyl-ethoxysilane in an excess of 13 mole equivalent and allowed to react. The epoxy reacts with the amino group of the SELP47K to form a $CH_2$—NH linkage. The reaction was carried out between 25-65° C., and the preferred reaction temperature was between 40-60° C. The reaction was carried out between 5-15 hours, and the preferred reaction time was between 10-15 hours.

The reaction product mixture was diluted with water, the buffer was exchanged with water, and excess unreacted silane was removed using a membrane dialyzer. The conjugation or grafting of the silanes to SELP was confirmed by SDS-PAGE analysis and total amine content analysis. The silylated-SELP conjugates were concentrated to 1% solution performed.

Example 4

A SELP47K-ChloroalkylSilane conjugate was prepared in the following manner: A SELP47K 1-10% solution of SELP47K, prepared in accordance with Example 1, was placed in 100 mM bicarbonate buffer having a pH 9.7 and was stirred to dissolve the protein polymer. 3-chloropropylmethyldimethoxysilane was placed in a pH 3.5 water solution and was stirred for 30 minutes at room temperature to hydrolyze the methoxy groups. The protein polymer solution was then mixed with the water solution of 3-chloropropylmethyldimethoxysilane in an excess of 13 mole equivalent and allowed to react. The reaction was carried out at a temperature between 25 to 55° C. The preferred reaction temperature was between 40 to 55° C. The reaction was carried out for between 5 to 15 hours, and the preferred reaction time was between 10 to 15 hours to allows the silylation to be completed. The reaction product mixture was diluted with water, the buffer was exchanged with water, and excess unreacted silane was removed using memebrane dialysis. The grafting of silane to the SELP47K was confirmed by SDS-PAGE analysis and total amine content analysis. The silylated-SELP47K was concentrated to 1% solution.

Example 5

A UV active p-hydroxy cinnamic acid was conjugated with SELP47K. The conjugation was performed by catalyzing amide bond formation between a lysine of SELP47K and a carboxyl group of p-hydroxy cinnamic acid. The amide bond formation was performed using 1-Ethyl-3-(3-Dimethylaminopropyl)carbodiimide Hydrochloride (EDC) and NHS (Product No. 24500), both available from Pierce Biotechnology, Rockford, Ill. SELP47K was dissolved at 1 mg/ml in an activation buffer (0.1 M MES, 0.5 M NaCl, pH 6.0). 0.4 mg EDC and 0.6 mg of NHS was added to 1 ml of the SELP47K solution and allowed to react for 15 minutes at room temperature. 1.4 μl of 2-mercaptoethanol was added to quench the EDC.

The p-hydroxy cinnamic acid was added to the reaction mixture at an equal mole-to-mole ratio with the SELP47K. The reaction mixture was allowed to react for 2 hours at room temperature. The reaction was quenched by adding hydroxylamine to a final concentration of 10 mM. Excess quenching reagent was removed by gel filtration. UV spectral analysis of the filtered product confirmed the grafting of the p-hydroxy cinnamic acid to SELP47K.

Example 6

Preparation and Verification of Quat 188-SELP47K Conjugate proceeded as follows. The Quat 188-SELP47K material was made by conjugation of Quat 188 (Dow Chemicals) to SELP47K at pH 10.7 in 24 hrs of reaction time. 50 g of SELP47K was dissolved in 900 ml of water & mixed with 100 ml Na Carbonate pH 11 (1M) and was filter sterilized using −0.22 micron filter. In parallel, the epoxide form of Quat 188 was made using 60 mls of Quat 188 in 240 ml of water and then adding 13 mls of 25% NaOH, to have a final pH of 11.5. Once pH 11.5 was reached, the Quat was allowed to react for 15 minutes at room temperature by mixing. Reaction of epoxy quat with the SELP47K was done by mixing it with 300 mls of quat preparation. The resulting pH was 10.7. The reaction mixture was placed in a 2L roller bottle and mixed overnight at 37 C on a roller bottle mixer rotating slowly. Confirmation of conjugation of SELP47K with quaternary ammonium salt was performed by Lys C (a commercial peptidase, Sigma chemical company) digestions (2 hrs) were performed on the material after ~20 hrs of reaction. The reaction mixture was then dialyzed (15K cut off membrane) to remove all unbound quat 188 and to reduce the pH. The conjugate was concentrated using YM30 membranes to a concentration between 30-60 mg/ml. The SELP-Quat were then lyophilized. The confirmation of the SELP47k-Quat conjugates was done through Endoproteinase Lys C digestion of SELP47K. Endo Lys C is an enzyme which cuts at lysines. SELP47K has 13 lysines spaced at regular intervals across the protein. Therefore, Endo lys C treatment of native SELP reduces the protein down to peptides ranging in MW from 4.5-6.3 KDa. However, if Quat 188 has been successfully conjugated to the lysines on SELP than they are no long susceptible to hydrolysis by endo Lys C. The degree of conjugation can be qualitatively determined by the resulting banding pattern on the gel. The SDS-PAGE gel analysis of lys-C treated SELP47K (control) and SELP47K-Quat conjugate confirms that the Quat 188 conjugate of SELP47K appears to be resistant to Lys-C digestion, indicating that the majority of the lysines have been modified with Quat 188 whereas Lys-C treatment of native SELP47K results in complete hydrolysis at all the lysines to the monomer.

Example 7

A fluorescent dye was conjugated with SELP47. Amide bond formation between a lysine of SELP47K and Fluorescein 5(6) isothiocyanate (FITC) was performed. 4 mg of FITC (available from Sigma Chemical) was dissolved in 2 ml of 100 mM sodium carbonate buffer pH 9 in a aluminum foil covered test tube. 1 ml of this solution was reacted with 3 ml of SELP47K 0.01% solution in the same carbonate buffer at 5° C. with slow mixing (50 rpm) using a magnetic stirrer for ninety minutes. An additional 0.5 ml of FITC reagent was added and further reacted with additional stirring for thirty minutes. To purify the FITC grafted SELP47K from the unreacted material, a PD-10 (BioRaD) desalting column was used. The PD-10 column was equilibrated with the same carbonate buffer prior to use. The reaction mixture (2 ml each) was loaded on to the column. The void volume was collected from the column containing the SELP47K-FITC conjugate. 10 ul of this SELP47K-FITC conjugate was assayed for estimating the specific activity (efficiency) of this conjugation by checking RFU (relative Fluorscence Unit) in a fluorescence plate reader (Molecular Devices, Fmax model) against bovine serum albumin protein control and BCA protein assay Kit (available from Pierce Biotechnology). The efficiency of conjugation was calculated and found to be above 95%.

Example 8

This example provides a method to conjugate the exemplary antimicrobial quaternary silicone, DC5700 (Dow Corning), to SELP47K, thereby creating a silicone-based antimicrobial-repeat sequence protein polymer conjugate, which may then be incorporated into desired surface material for antimicrobial protection. Conjugation of DC5700 to SELP47K was accomplished through a two-step process in which the DC5700 is attached to SELP47K via an epoxysilane (ES) linker. The epoxysilane was first conjugated to the lysines on SELP47K (50 mg) via an epoxy group on the silane. The epoxysilane used in the reactions is (3-glycidoxypropyl) methyl dimethyoxysilane (4-8 ul) (Aldrich Chemical Company). This reaction was carried out at 37° C. overnight, using 1 ml of 0.1 molar sodium carbonate/bicarbonate buffer pH 9.5. The reaction mixture was then desalted into water using a NAP5 desalting column ending with 400 μl of SELP47K-ES conjugate. Conjugation of epoxysilane to the beta amino groups of lysines of SELP47K was verified using endopeptidase lysC and SDS PAGE gel electrophoresis analysis. The next step involved a silicone condensation reaction between the hydroxy silane groups on the ES with those on DC5700. The 400 μl desalted SELP47K-ES samples were reacted with 4 μl of DC700 (Ageis Chemicals) at pH 8 using 2 μl of 1 molar NaOH, overnight at room temperature. The reaction mixture was desalted again to make sure unconjugated DC5700 separated out. The verification of DC5700 conjugation with SELP47K was pursued using endopeptidase lysC, SDS-PAGE gel and size exclusion chromatography. The conjugated material was then tested for its antimicrobial efficacy using the microorganism Bacillus subtilis. The results suggest that the conjugated material exhibits antimicrobial efficacy similar to that of DC5700 alone.

Example 9

A SELP47K-carboxysiloxane conjugate may be prepared in accordance with the following steps. A 1-10% solution of SELP47K may be placed in 100 mM phosphate buffer, pH 7.0, and stirred to dissolve all the protein polymer. This protein polymer solution may then be mixed with monocarboxyldecyl terminated polydimethylsiloxane in an excess of 13 mole equivalent and a lipase enzyme. The reaction may be carried out at about 37° C. The reaction may be carried out for between 5 to 15 hours. The preferred reaction time may be between 10 to 15 hours. After the reaction, the reaction product mixture may be diluted with water, the buffer may be exchanged with water, and excess unreacted siloxane may be removed. The grafting of the siloxane to SELP47K may be confirmed by SDS-PAGE analysis and total amine content analysis. The silylated-SELP47K may be concentrated to 1% solution and stored.

Example 10

An allyl cinnamic acid fragrance molecule SELP47K conjugate may be prepared according to the following steps. The conjugation may be performed by catalyzing amide bond formation between a lysine of SELP47K and a carboxyl group of allyl cinnamic acid. The amide bond formation may be performed using 1-Ethyl-3-(3-Dimethylaminopropyl)carbodimide Hydrochloride (EDC) and NHS (Product No. 24500), both available from Pierce Biotechnology, Rockford, Ill. SELP47K may be dissolved at 1 mg/ml in an activation buffer (0.1 M MES, 0.5 M NaCl, pH 6.0). 0.4 mg EDC and 0.6 mg of NHS may be added to 1 ml of the SELP47K solution and allowed to react for 15 minutes at room temperature. 1.4 μl of 2-mercaptoethanol may be added to quench the EDC. The allyl cinnamic acid may be added to the reaction mixture at an equal mole-to-mole ratio with the SELP47K. The reaction mixture may be allowed to react for 2 hours at room temperature. The reaction may be quenched by adding hydroxylamine to a final concentration of 10 mM. Excess quenching reagent may be removed by gel filtration. The conjugated material may have a UV spectral signature that is either red or blue shifted in comparison to the UV spectral signature of the unreacted allyl cinnamic acid.

Example 13

An ascorbic acid (vitamin C) molecule SELP47K conjugate may be prepared according to the following steps. The conjugation may be performed by catalyzing amide bond formation between a lysine of SELP47K and a carboxyl group of ascorbic acid. The amide bond formation may be performed using 1-Ethyl-3-(3-Dimethylaminopropyl)carbodiimide Hydrochloride (EDC) and NHS (Product No. 24500), both available from Pierce Biotechnology, Rockford, Ill. SELP47K may be dissolved at 1 mg/ml in an activation buffer (0.1 M MES, 0.5 M NaCl, pH 6.0). 0.4 mg EDC and 0.6 mg of NHS may be added to 1 ml of the SELP47K solution and allowed to react for 15 minutes at room temperature. 1.4 μl of 2-mercaptoethanol may be added to quench the EDC. The ascorbic acid may be added to the reaction mixture at an equal mole-to-mole ratio with the SELP47K. The reaction mixture may be allowed to react for 2 hours at room temperature. The reaction may be quenched by adding hydroxylamine to a final concentration of 10 mM. Excess quenching reagent may be removed by gel filtration. The conjugated material may have a UV spectral signature that is either red or blue shifted in comparison to the UV spectral signature of the unreacted ascorbic acid.

Example 12

Construction, analysis, and verification of AMP-SELP47K Conjugates proceeded as follows. Two previously described AMPs were chosen, MBI-28 WKLFKKIGIGAVLKVLT-TGLPALKLTK (Gough, M. et. al. *Infect Immun.* 1996 December; 64(12): 4922-7) and Cecropin A-Meletin hybrid KWKLFKKIGAVLKVL. AMP peptide sequences were back-translated into *Escherichia coli* DNA coding sequences using Vector NTI software (Informax). A hexamer tandem repeat was designed for each AMP, individual AMPs being linked by glycine residue hexamers. Codon redundancy in *E. coli* was exploited in order to minimize the repetitive nature of the hexamer sequence while avoiding rare codons. 5' and 3' DNA sequences were added to the hexamers rendering the hexamer amenable to subcloning into the N-terminus or the C-terminus of SELP47K coding sequence with in frame expression. In addition, the coding sequence for a thrombin protease recognition site was included in the 5 prime region of the hexamer such that AMPs may be cleaved in vitro from C-terminal fusions. Each AMP hexamer construct had a unique restriction enzyme cleavage site included within its sequence to facilitate screening, identification of correct constructs. AMP hexamer constructs were manufactured by Blue Heron Biotechnology (Bothell, Wash.) using artificial gene synthesis technology and were provided in a pUC-based plasmid.

SELP47K is encoded by a 2652 base pair sequence present on a pUC based plasmid under the control of a heat inducible lambda Pr promoter. The selectable marker for kanamycin antibiotic resistance is present on this plasmid. A unique BglII restriction site was engineered into the 3' "tail" of the SELP47K coding sequence using Quick Change™ methodology (Stratagene). AMP hexamer construct plasmids provided by Blue Heron Biotechnology were subjected to restriction enzyme digestion using BglII enzyme (Roche) and the resulting hexamer cassettes were excised and purified from agarose gels using a commercial kit (Qiagen). SELP47K plasmid was cut with BglII enzyme, purified from agarose gels, and dephosphorylated using calf intestinal phosphatase (New England Biolabs). Hexamer cassettes were subcloned into the SELP47K 3' BglII site using T4 DNA ligase (New England Biolabs). Subcloning was performed using *E. coli* TOP10 chemically competent cells (Invitrogen). Recombinant SELP47K plasmids were screened for the presence of hexamer cassettes using plasmid isolation and restriction enzyme analysis/gel electrophoresis. DNA sequencing was used to confirm the presence of AMP hexamer in the correct orientation.

Insertion of the AMP hexamers into SELP47K 5' "head" was performed as described above except that a unique BamHI site was used. AMP hexamer constructs contain a 3' TAA stop codon as they were designed primarily for C-terminal insertion. Quick Change was used to remove the T residue from the stop codon prior to subcloning into SELP47K. Removal of the T residue had the concomitant effect of rendering the subsequent SELP47K coding region in-frame. Successful constructs were further verified for correctness using restriction enzyme/gel electrophoresis analysis. Plasmids were used to transform *E. coli* MM294 using LB plates containing 50 ppm kanamycin. Single colonies were picked and grown in 60 ml TM2 (recipe)+2% glucose, 50 ppm kanamycin in 500 ml fluted Erlenmeyer flasks, 30° C., 250 rpm, 16 hrs. Cell culture was supplemented with glycerol (10% v/v), and 1.5 ml aliquots were placed in cryovials and stored at −80° C. Random vials were tested for contamination by incubating 10 μl inoculating loopfuls on LA+1.6% skim milk plates, 37° C., 16 hrs. Integrity of the plasmids were also confirmed using plasmid purification and analysis using restriction enzyme digestion/gel electrophoresis as well as DNA sequencing. Frozen cryovials were used as seed stocks for subsequent culturing, protein production.

Seed vials were used for fermentation of AMP-SELP47K protein polymers. Two strains tested for fermentation were MM294/pSELP0888 (CAM-SELP47K, SEQ. ID. NO. 32) and MM294/pSELP1064 (MBI-SELP47K, SEQ. ID. NO. 33). Both strains were inoculated with a defined TM2 medium and batched glucose. *E. coli* fermentation was continued with a feed of 2 g/min of glucose upon consumption of batched glucose till cells in the fermentors grew up to an OD of 60. The expression of AMP-SELP47K protein polymer was started with temperature induction by raising the fermentation temperature to 40 C. Both fermentations behaved similarly. Growth rates were nearly the same. Cell pastes were harvested by centrifuging fermentation broth after CER drop.

Purification of AMP-SELP47K fusion proteins was performed by first taking the cell paste in 1:2 ratio in DI water, followed by homogenizing the cells using French-Press at 8000 PSI. Homogenized cells were mixed with 0.1-10% PEI (polyethyleneimine) to flock-out cell-debris. The cell-debris was removed by centrifugation. Cell-extract generated from centrifugation was mixed with ammonium sulfate (10-25% saturation) to precipitate AMP-SELP fusion protein polymer. Precipitated AMP-SELP47K fusion polymer was separated from the rest of mother liquor and dissolved in MQ water. AMP-SELP47K fusion polymer was purified for its salts contents by dialysis and then lyophilized as solid powder for storage. Analysis of purified AMP-SELP47K was carried out using SDS gel electrophoresis as well as mass spectrometry.

Antimicrobial activity of culture supernatants and purified samples was assayed as follows: Samples of interest as well as AMP positive controls and purified SELP47K negative control were used. Positive controls were serial diluted 1:2 from 200 μg/ml to 1.56 μg/ml in Luria Broth (LB media) and consisted of cecropin A (Sigma), and MBI-28 (synthesized in-house). *Escherichia coli* MG1655 and *Bacillus subtilis* 168 were used as Gram-negative and Gram-positive microbial targets. Five ml overnight cultures, grown from single colonies in LB, were diluted 1:250 in Terrific Broth (TB) and 100 μl aliquots were placed in duplicate in wells of sterile flat bottom 96 well microtiter plates. Uninoculated TB was also aliquoted as control. Perimeter wells were not used but were instead filled with media so as to minimize "edge effects". 100 μl of the above dilutions of controls and samples were mixed with diluted bacterial aliquots as well as with 100 μl of sterile TB as negative controls/blanks. Plates were incubated, humidified, at 37 C, 250 rpm. $OD_{600}$ for each well was monitored hourly using a plate reader.

Culture supernatant samples from post-induction timepoints from a fermentation of Cecropin A-Meletin (CAM) fused to the N-terminus of SELP47K were tested for growth inhibition of *E. coli* and *B. subtilis*. The results indicated that inhibition of growth of both strains increases dramatically after induction. Purified CAM-SELP47K (SEQ. ID. NO.32) and MBI-SELP47K (SEQ. ID. NO. 33) biomaterials were similarly tested for their antimicrobial activity. Lyophilized material was dissolved in water at 1.25 mg/ml and used in a test-tube based assay performed as follows: *Bacillus subtilis* 168 and *Escherichia coli* MG1655 were each grown from single colonies in 5 ml volumes of LB in test tubes, 37° C., 250 rpm, 16 hrs. Cultures were diluted 1:500 in Terrific broth. Equal volumes of diluted culture and purified AMP-SELP fusions described above were combined in sterile glass test-tubes (1 ml total volume in 5 ml tubes), in duplicate, and incubated at 37° C., 250 rpm. Purified SELP47K was used as a negative control. After 4 hours growth was clearly visible in the tubes containing SELP47K while tubes containing AMP-SELP fusions had significantly less growth indicating growth inhibitory and antimicrobial properties of the fusion proteins.

Example 14

Construction, analysis, and verification of SELP47K-GFP (SEQ. ID. NO. 34) conjugate proceeded as follows. A protein fusion of green fluorescent protein (GFP) and silk elastin protein polymer (SELP47K) in *E. coli* was produced using molecular biology and fermentation techniques. Briefly, a gene encoding GFP was cloned into the 5 prime end (N-terminus) of the gene encoding SELP47K, for in-frame translation. This gene construct was expressed with a lambda Pr expression vector in *E. coli* MM294 at shake flask scale. Plasmid pGFP and its DNA sequence were obtained from Clontech. After methods similar to those discussed in the previous example, resultant seed vials were checked for microbial contamination and stored at −80° C., and used for fermentation of GFP-SELP47K protein polymers. Purification of GFP-SELP47K fusion proteins was performed similarly to Example 13. Analysis of purified GFP-SELP47K was carried out using SDS gel electrophoresis as well as mass spectrometry to confirm the formation of fusion polymer. GFP-SELP47K conjugate protein polymer was probed for fluorescence excitation and emission spectrum of GFP-SELP47K protien polymer biomaterial and its surface filming characteristics as follows: the emission spectra of purified GFP-SELP47K were recorded and compared to purified SELP47K at the same protein concentration level using a fluoresence spectrophotometer (Spectromax Gemini, Molecular Devices). Excitation wavelengh for this measurement was 395 nm and emission spectrum was recorded (450-600 nm). The green fluoresence emission of GFP-SELP47K was similar to that of native wild-type GFP of jellyfish (Clonetech) at 509 nm.

Example 14

Construction, analysis and verification of the SELP47K-CPB (SEQ. ID. NO. 37) conjugate proceeded using the same general techniques as discussed in previous Examples 12 and 13. Cellulose binding peptide (CBP) sequence was obtained in-house using PCR driven phage display. The sequence used was TTHPQMLWQMST. CBP peptide sequence was back-translated into *Escherichia coli* DNA coding sequence using Vector NTI software (Informax). A hexamer tandem repeat was designed using CBP DNA sequence, individual CBPs being linked by glycine residue quatramers. Codon redundancy in *E. coli* was exploited in order to minimize the repetitive nature of the hexamer sequence while avoiding rare codons. 5' and 3' DNA sequences were added to the hexamer rendering the hexamer amenable to subcloning into the N-terminus or the C-terminus of SELP47K coding sequence with in-frame expression. The CBP hexamer construct had a unique restriction enzyme cleavage site included within its sequence to facilitate screening, identification of correct constructs. CBP hexamer construct was manufactured by Blue Heron Biotechnology (Bothell, Wash.) using artificial gene synthesis technology and was provided in a pUC-based plasmid. SELP47K is encoded by a 2652 base pair sequence present on a pUC based plasmid under the control of a heat inducible lambda Pr promoter. The selectable marker for kanamycin antibiotic resistance is present on this plasmid. A unique BglII restriction site was engineered into the 3' "tail" of the SELP47K coding sequence using Quick Change™ methodology (Stratagene). CBP hexamer construct plasmid provided by Blue Heron Biotechnology was subjected to restriction enzyme digestion using BglII enzyme (Roche) and the resulting hexamer cassette was excised and purified from agarose gels using a commercial kit (Qiagen). SELP47K plasmid was cut with BglII enzyme, purified from agarose gels, and dephosphorylated using calf intestinal phosphatase (New England Biolabs). The hexamer cassette was subcloned into the SELP47K 3' BglII site using T4 DNA ligase (New England Biolabs). Subcloning was performed using *E. coli* TOP10 chemically competent cells (Invitrogen). Recombinant SELP47K plasmids were screened for the presence of hexamer cassette using plasmid isolation and restriction enzyme analysis/gel electrophoresis. DNA sequencing was used to confirm the presence of CBP hexamer in the correct orientation. Insertion of the CBP hexamer into SELP47K 5' "head" was performed as described above except that a unique BamHI site was used. The CBP hexamer construct contains a 3' TAA stop codon as it was designed primarily for C-terminal insertion. Quick Change was used to remove the T residue from the stop codon prior to subcloning into SELP47K. Removal of the T residue had the concomitant effect of rendering the subsequent SELP47K coding region in-frame. Successful constructs were further verified for correctness using restriction enzyme/gel electrophoresis analysis. Plasmid was used to transform *E. coli* MM294 using LB plates containing 50 ppm kanamycin. Single colonies were picked and grown in 60 ml TM2 (recipe)+2% glucose, 50 ppm kanamycin in 500 ml fluted Erlenmeyer flasks, 30° C., 250 rpm, 16 hrs. Cell culture was supplemented with glycerol (10% v/v), and 1.5 ml aliquots were placed in cryovials and stored at −80° C. Random vials were tested for contamination by incubating 10 ul inoculating loopfuls on LA+1.6% skim milk plates, 37° C., 16 hrs. Integrity of the plasmid was also confirmed using plasmid purification and analysis using restriction enzyme digestion/gel electrophoresis as well as DNA sequencing. Frozen cryovials were used as seed stocks for subsequent culturing, protein production.

Example 15

The SELP47K conjugate construct, CBP-SELP47K-S2E1 in which all polymer subunits contain one cotton-binding peptide sequence was made as follows: Artificial gene synthesis was used to create a 2 subunit version of the desired construct in which each identical subunit contains a unique non-palindromic restriction site. Specifically, SELP47K subunits contained the linear cotton binding peptide (TTHPQMLWQMST) incorporated between the C-terminal end of the silk region and the N-terminal end of the elastin region (region S2E1). A BsgI restriction enzyme cleavage site was designed within each subunit. Gene construction was carried out by Blue Heron Biotechnology (Bothell, Wash.). DNA was digested with BsgI which resulted in the release of a single subunit per molecule. Resulting modified SELP monomers as well as plasmid vector were purified from agarose gels and concentrated using a Spin Vac. Monomers were self ligated using T4 DNA ligase (New England Biolabs) as per manufacturer's instructions overnight at 16 C (FIG. 3). Original purified vector was added to ligation mix with additional fresh ligase and incubated at 16 C for an additional 24 hrs. Ligation mix was used to transform *E. coli* TOP10 cells (Invitrogen) as per manufacturer's instructions. Resulting transformants were used to inoculate culture tubes containing 5 ml Luria broth and appropriate antibiotic. Tubes were incubated for 16 hrs, 37 C, 250 rpm. Plasmids were purified from resulting cultures using a Plasmid Miniprep kit (Qiagen). Complete SELP47K-CBP conjugate inserts were excised from vector by digestion with EcoRV and BamHI restriction enzymes and sized using agarose gel elecrophoresis in order to identify constructs containing the desired 13 total subunits. Appropriate SELP47K-CBP conjugate gene constructs were subcloned into vector containing lambda Pr promoter and transformed into production host *E. coli* MM294. Prepared seed vials were stored at −80 C. Seed vials were used for fermentation of CBP-SELP47K protein polymers. Strain tested for fermentation run 20031115 and 20031211 was MM294/pSELP0845 (CBP{L12}-SELP47K). *E. coli* strain was inoculated with a defined TM2 medium and batched glucose. *E. coli* fermentation was continued with a feed of 2 g/min of glucose upon consumption of batched glucose till cells in the fermentors grew up to an OD of 60. The expression of CBP-SELP47K protein polymer was started with temperature induction by raising the fermentation temperature to 40 C. Both fermentations behaved similarly. Growth rates were nearly the same. Cell pastes were harvested by centrifuging fermentation broth after 20% drop in CER and with no further rise in OD. Purification of CBP-SELP47K fusion proteins was performed by first taking the cell paste in 1:2 ratio in DI water, followed by homogenizing the cells using French-Press at 8000 PSI. Homogenized cells were mixed with 0.1%-10% PEI (polyethyleneimine) to flock-out cell-debris. The cell-debris was removed by centrifugation. Cell-extract generated from centrifugation was mixed with ammonium sulfate (10-25% saturation) to precipitate CBP-SELP fusion protein polymer. Precipitated CBP-SELP47K fusion polymer was separated from the rest of mother liquor and dissolved in either MQ water or with the use of chiotropic agents such as urea, guanidinium hydrochloride. CBP-SELP47K fusion polymer(s) was purified for its salts contents by dialysis and then lyophilized as solid powder for storage. Analysis of purified CBP-SELP47K was carried out using SDS gel electrophoresis as well as mass spectrometry to confirm the formation of fusion polymer.

CBP-SELP47K fusion proteins were assayed for cellulose binding properties as follows: the cotton binding properties of CBP-SELP47K were compared to SELP47K in two different assays. One assay was a dose response assay in which the cotton (substrate) concentration was held constant and the SELP47K concentration varied. The second experiment was one in which the cotton concentration varied and the SELP47K concentration was held constant. All binding studies were carried out in European laundry detergent. The procedures and results are as follows: each experiment consisted of three parts 1) preparation of the cotton swatches and detergent 2) incubation of SELP47K with cotton in European detergent 3) determination of the amount of SELP47K bound to the cloth. 1) A circular ¼ inch dye was used to punch out cotton microswatches from EMPA 221 unsoiled cotton fabric (Testfabrics). 28 microswatches were washed for 15 minutes at 37 C in 10 ml of filtered WFK-1 European laundry detergent (3.5 g/L, AATCC—American Association of Textile Chemists and Colorists) containing 15 grains per gallon (gpg) hardness (1.85 mM $CaCl_2$.0.54 mM $MgCl_2$). The samples were washed using a DYNAL rotating mixer (40 RPM). The swatches were then rinsed in 3 gpg water hardness (0.37 mM $CaCl_2$, 0.108 mM $MgCl_2$) at 37 C for 5 minutes (40 RPM) and then blotted dry on paper towels. 2) Three concentrations of the SELP proteins (CBP-SELP47K: 1.25, 0.84, 0.45 & 0 mg/ml: SELP47K 1.35, 1.0, & 0.58 mg/ml) were made up in filtered WFK-1 detergent (3.5 g/l, 15 gpg hardness). 900 ul of the diluted SELP proteins was then added to a 1.5 ml eppendorf tube containing 4 prewashed cotton microswatches. The tubes were mixed on a DYNAL rotary mixer (30 min, 40 C, 400 RPM). The swatches were then rinsed 3 times in 1 ml of water containing 3 gpg hardness (5 min, room temperature, shaking). 3) The swatches, supernatant and rinses were all analyzed for the presence of SEL47K using the BCA protein assay (Pierce). The BCA assay was modified slightly in order to analyze the solid cotton swatches. The reaction was carried out as follows: 300 ul of the BCA assay reagent was incubated with 1 cotton swatch from each reaction. A BSA standard curve was assayed at the same time and used to quantify the amount of protein bound to the cloth. The swatches and BSA were incubated with the BCA reagent for ~30 minutes, in eppendorf tubes. At the end of the 30 minutes the swatches were mixed well and then 200 µl aliquots of the supernatant was then read at 562 nm. The concentration of protein bound to the swatch was determined based off of the BSA standard curve. The cotton binding activity of CBP-SELP47K was compared to that of native SELP47K and revealed that the CBP-SELP47K targets and binds SELP47K to the cotton to a much greater extent than does native SELP47K. In order to confirm that the protein which bound to the cloth was CBP-SELP47K, the bound protein was eluted from the cotton and run on a SDS gel. This was accomplished by boiling the bound swatch in NuPage LDS sample buffer 4× (Invitrogen) at 95 C for 10 minutes, and running the supernatant on a SDS gel (invitrogen, on a 4-12% bis-tris NuPage gel).

A second binding experiment was run which explored the cotton binding of Hexamer CBP-SELP47K at different substrate concentrations. The swatches were prepared in the same manner as described in the previous experiment. This time 40 swatches were washed. The washed swatches were placed in a 48 well microtiter plate such that two wells contained 0, 1, 2, 3, 4, & 5 swatches respectively. SELP47K stock solutions (SELP47K: 1 mg/ml, CBP-SELP47K, 0.75 mg/ml) were made up in filtered WFK-1 European laundry detergent (3.5 g/l, 15 gpg hardness). 200 µl of the SELP stock solutions was added to the wells of the microtiter plate, which contained the washed swatches. The SELP proteins were then incubated with the swatches (40 C, 30 minutes, 240 RPM). The supernatant was then removed from the wells and the swatches rinsed 3× in 3 gpg water (600 µl, 5 minutes shaking). The swatches were analyzed in the same manner as described in the previous binding experiment. The amount of CBP-SELP47K which bound to cotton increased with increasing cotton concentration. The same amount of CBP-SELP47k binds to each swatch regardless of the number of swatches present in the reaction. This indicates that CBP-SELP47K has saturated all the binding sites available on the cotton swatches. In all cases the amount of CBP-SELP47K, which bound to the cotton is much greater than that of native SELP47K. The CBP-SELP47K-S2E1 (SEQ. ID. NO. 35) conjugate shows an excellent and improved binding to cotton because the cotton binding peptide is capable of being provided periodically throughout the conjugate. More than 10% of this cotton S2E1-SELP47K (CBP-SELP47K-S2E1) (SEQ. ID. NO. 35) conjugate was bound to the cotton as tested using the above described protocol.

Example 17

Construction, analysis and verification of the SELP47K-P4 (SEQ. ID. NO. 36) conjugate proceeded as follows. SELP constructs in which all polymer subunits contain additional P4 (ALSYP) peptide sequences were made as follows: Artificial gene synthesis was used to create a 2 subunit version of the desired construct in which each identical subunit contains a unique non-palindromic restriction site. Specifically, SELP subunits contained either BBI derived P4 sequences (Seq ALSYP) incorporated in two places per subunit, flanking the silk region, incorporated between the C-terminal end of the silk region and the N-terminal end of the elastin region. A BsgI restriction enzyme cleavage site was designed within each subunit. Gene construction was carried out by Blue Heron Biotechnology (Bothell, Wash.). DNA was digested with BsgI which resulted in the release of a single subunit per molecule. Resulting modified SELP monomers as well as plasmid vector were purified from agarose gels and concentrated using a Spin Vac. Monomers were self ligated using T4 DNA ligase (New England Biolabs) as per manufacturer's instructions overnight at 16 C. Original purified vector was added to ligation mix with additional fresh ligase and incubated at 16 C for an additional 24 hrs. Ligation mix was used to transform *E. coli* TOP10 cells (Invitrogen) as per manufacturer's instructions. Resulting transformants were used to inoculate culture tubes containing 5 ml Luria broth and appropriate antibiotic. Tubes were incubated for 16 hrs, 37 C, 250 rpm. Plasmids were purified from resulting cultures using a Plasmid Miniprep kit (Qiagen). Complete SELP inserts were excised from vector by digestion with EcoRV and BamHI restriction enzymes and sized using agarose gel elecrophoresis in order to identify constructs containing the desired 13 total subunits. Appropriate SELP gene constructs were subcloned into vector containing lambda Pr promoter and transformed into production host *E. coli* MM294. Prepared seed vials were stored at −80 C. Seed vials were used for fermentation of P4-SELP47K protein polymers. Strain tested for fermentation run 20040236 was MM294/pSELP01472 (P4-SELP47K). *E. coli* strain was inoculated with a defined TM2 medium and batched glucose. *E. coli* fermentation was continued with a feed of 2 g/min of glucose upon consumption of batched glucose till cells in the fermentors grew up to an OD of 60. The expression of P4-SELP47K protein polymer was started with temperature induction by raising the fermentation temperature to 40 C. Both fermentations behaved similarly to that of SELP47K fermentation and growth rates were nearly the same. Cells grew well prior to induction and after. Cell pastes were harvested by centrifuging fermentation broth after 20% drop in CER and with no further rise in OD. Purification of P4-SELP47K fusion proteins was performed by first taking the cell paste in 1:2 ratio in DI water, followed by homogenizing the cells using French-Press at 8000 PSI. Homogenized cells were mixed with 0.1%-10% PEI (polyethyleneimine) to flock-out cell-debris. The cell-debris was removed by centrifugation. Cell-extract generated from centrifugation was mixed with ammonium sulfate (10-25% saturation) to precipitate P4-SELP fusion protein polymer. Precipitated P4-SELP47K fusion polymer was separated from the rest of mother liquor and dissolved in in either MQ water or with the use of chiotropic agents such as urea, guanidinium hydrochloride. P4-SELP47K fusion polymer(s) was purified for its salts contents by dialysis and then lyophilized as solid powder for storage. Analysis of purified P4-SELP47K was carried out using SDS gel electrophoresis as well as mass spectrometry to confirm the formation of fusion polymer. P4-SELP47K fusion proteins were assayed for properties as follows: A fibroblast cell culture model was used to assess the ability of the test materials to exert a protective effect by promoting cell survival after UVB exposure. P4-SELP47K biomaterial was tested at three concentrations in triplicate. Human dermal fibroblasts was exposed to a dose of UVB light (approximately 50 mj/cm$^2$), which has been shown to reduce the number of viable cells by 50% at 48 hours post UV exposure. Immediately after the UVB exposure cells was treated with either P4-SELP conjugate materials, 20 µM Trolox (an antioxidant, used as a positive control), or left untreated (untreated controls). Changes in cell viability will then be determined 48 hours later via an MTT assay. The MTT assay is a calorimetric analysis of the metabolic activity of the cell, which is a reflection of cell viability. Viable cells can take up MTT, which is then reduced by mitochondria resulting in the formation of insoluble purple formazin crystals. These crystals are then extracted from the cells with isopropanol and quantified spectrophotometrically. The intensity of the purple color is directly proportional to the number of viable cells and inversely proportional to the toxicity of the test material. Fibroblasts were seeded into the individual wells of a 96 well plate in 100 µl of Fibroblast Growth Medium (FGM) and incubated overnight at 37±2° C. and 5±1% $CO_2$. On the following day the media was removed via aspiration to eliminate any non-adherent cells and replaced with 100 µl of fresh FGM. The cells were grown until confluent, with a media change every 48 to 72 hours. An UVLM-26 lamp was used as the source of UVB light. UV light intensity was measured using a UVX radiometer coupled to a UVB sensor probe (UV Products) to determine the time required to deliver an approximate dose of 50 mj/cm$^2$. Prior to UVB exposure the FGM was replaced with 100 µl of PBS. After exposure the PBS was removed and replaced with FGM supplemented with either the P4-SELP conjugate, 20 µM Trolox, or left unsupplemented. A duplicate set of cells were also be prepared and treated as described above with the exception that they were exposed to UVB light. This second set was used to assess any changes on cell viability induced by the test materials alone. The non-UVB exposed cells treated with unsupplemented FGM were used to represent 100% cell viability. At the end of the 48-hour incubation period the cells were photographed to record any changes in cell morphology. Also, after the 48-hour incubation, the cell culture medium was removed and the fibroblasts were washed with PBS to remove any remaining test material. After the final wash, 100 µl of DMEM supplemented with 0.5 mg/ml MTT was added to each well and the cells were incubated for 1 to 2 hours at approx. 37±2° C. and 5±1% $CO_2$. After the incubation, the DMEM/MTT solution was removed and the cells were washed again once with PBS and then 50 µl of isopropyl alcohol was added to the well to extract the purple formazin crystals. The 96-well plate was then be read at 540 nm using isopropyl alcohol as a blank. The mean MTT absorbance value for the negative control cells was calculated and used to represent 100% value for cell number. The individual MTT values from the cells undergoing the various treatments was then divided by the mean value for the negative control cells and expressed as a percent to determine the change in cell number caused by each treatment. SELP47K-P4 conjugate results in 100% viability improvement of UV treated human fibroblast cells.

Example 18

Construction of P4 and Linear CBP-SELP conjugates proceeded as follows. SELP constructs in which all polymer subunits contain additional peptide sequences were made as follows: Artificial gene synthesis was used to create a 2 subunit version of the desired construct in which each identical subunit contains a unique non-palindromic restriction site. Specifically, SELP subunits contained either BBI P4 sequences incorporated in two places per subunit, flanking the silk region, or the linear cotton binding peptide incorporated between the C-terminal end of the silk region and the N-terminal end of the elastin region (region S2E1). A BsgI restriction enzyme cleavage site was designed within each subunit. Gene construction was carried out by Blue Heron Biotechnology (Bothell, Wash.). DNA was digested with BsgI which resulted in the release of a single subunit per molecule. Resulting modified SELP monomers as well as plasmid vector were purified from agarose gels and concentrated using a Spin Vac. Monomers were self ligated using T4 DNA ligase (New England Biolabs) as per manufacturer's instructions overnight at 16 C (FIG. 1). Original purified vector was added to ligation mix with additional fresh ligase and incubated at 16 C for an additional 24 hrs. Ligation mix was used to transform E. coli TOP 10 cells (Invitrogen) as per manufacturer's instructions. Resulting transformants were used to inoculate culture tubes containing 5 ml Luria broth and appropriate antibiotic. Tubes were incubated for 16 hrs, 37 C, 250 rpm. Plasmids were purified from resulting cultures using a Plasmid Miniprep kit (Qiagen). Complete SELP inserts were excised from vector by digestion with EcoRV and BamHI restriction enzymes and sized using agarose gel elecrophoresis in order to identify constructs containing the desired 13 total subunits. Appropriate SELP gene constructs were subcloned into vector containing lambda Pr promoter and transformed into production host E. coli MM294. Prepared seed vials were stored at −80 C.

What is claimed is:

1. Biomolecular conjugates comprising the conjugation product of a repeat sequence protein polymer comprising SEQ ID NO. 19 and at least one active agent, wherein the at least one active agent is selected from the group consisting of: silicones, fragrances, dyes, tints, UV active agents, sunscreens, lanolin, vitamins, bleaches, thickening agents, enzymes, antimicrobials, preservatives, and combinations thereof.

2. The biomolecular conjugates as recited in claim 1, wherein the at least one active agent comprises a silicone.

3. The biomolecular conjugates as recited in claim 2, wherein the silicone is selected from the group consisting of: silicones comprising an epoxy functional group, polydimethyl siloxanes, silicone resins, silicone surfactants, alkyl modified silicones, gum-silicone fluid blends, phenyl silicone fluids, dimethyl silicone fluids, quaternized ammonium salts of suitable silicones, silicones comprising one or more amino functional groups, and combinations thereof.

4. A personal care composition comprising the biomolecular conjugates as recited in claim 1 with a carrier or excipient.

5. The personal care composition as recited in claim 4 wherein the composition is a hair care composition, a skin care composition, a nail care composition, a cosmetic composition, an oral care composition, or an over-the-counter pharmaceutical composition.

6. The personal care composition as recited in claim 4 wherein the biomolecular conjugates comprise from about 0.001% to about 10% by weight of the composition.

7. The personal care composition as recited in claim 4 wherein the biomolecular conjugates comprise from about 0.01% to about 5% by weight of the composition.

8. The personal care composition as recited in claim 4 wherein the biomolecular conjugates comprise from about 0.01% to about 1% by weight of the composition.

9. A process for making a personal care composition comprising combining a biomolecular conjugate with an acceptable carrier or excipient to obtain a personal care composition, wherein the biomolecular conjugate comprises a conjugation product of a repeat sequence protein polymer comprising SEQ ID NO. 19 and at least one active agent, wherein the at least one active agent is selected from the group consisting of: silicones, fragrances, dyes, tints, UV active agents, sunscreens, lanolin, vitamins, bleaches, thickening agents, enzymes, antimicrobials, preservatives, and combinations thereof.

10. A method of producing a biomolecalar conjugate comprising a fusion protein conjugate comprising a conjugation product of a repeat sequence protein polymer comprising SEQ ID NO. 19 and at least one active agent selected from the group consisting of: silicones, fragrances, dyes, tints. UV active agents, sunscreens, lanolin, vitamins, bleaches, thickening agents, enzymes, antimicrobials, preservatives, and combinations thereof, the method comprising:

selecting the repeat sequence protein polymer and the active agent suitable for a desired application;

obtaining a gene encoding the repeat sequence protein polymer and a gene encoding the at least one active agent; constructing a conjugate gene from the gene encoding the repeat sequence protein polymer and the gene encoding the at least one active agent comprising a protein or peptide;

expressing the conjugate gene to form an expression product comprising the fusion protein conjugate; fermenting the expression product comprising the fusion protein conjugate; and purifying the fusion protein conjugate.

11. The method as recited in claim 10 comprising at least two active agents.

12. The method as recited in claim 10 wherein the at least one active agent comprises a protein or a peptide comprising an antimicrobial peptide, a UV active agent, a cotton binding peptide, green fluorescent protein, or a combination thereof.

13. A repeat sequence protein polymer comprising the biomolecular conjugate as recited in claim 1.

14. Biomolecular conjugates comprising the conjugation product of a repeat sequence protein polymer having the sequence SEQ. ID NO. 19 and at least one active agent selected from the group consisting of silicones, fragrances, dyes, tints, UV active agents, sunscreens, lanolin, vitamins, bleaches, thickening agents, enzymes, antimicrobials, preservatives, and combinations thereof.

15. The biomolecular conjugates as recited in claim 14, wherein the at least one active agent comprises a silicone.

16. The biomolecular conjugates as recited in claim 14, wherein the silicone is selected from the group consisting of: silicones comprising an epoxy functional group, polydimethyl siloxanes, silicone resins, silicone surfactants, alkyl modified silicones, gum-silicone fluid blends, phenyl silicone fluids, dimethyl silicone fluids, quaternized ammonium salts of suitable silicones, silicones comprising one or more amino functional groups, and combinations thereof.

17. A personal care composition comprising the conjugation product of a repeat sequence protein polymer having the sequence SEQ. ID NO. 19; at least one active agent selected from the group consisting of silicones, fragrances, dyes, tints, UV active agents, sunscreens, lanolin, vitamins, bleaches, thickening agents, enzymes, antimicrobials, preservatives, and combinations thereof; and a cater or excipient.

18. The personal care composition as recited in claim 17 wherein the composition is a hair care composition, a skin care composition, a nail care composition, a cosmetic composition, an oral care composition, or an over-the-counter pharmaceutical composition.

\* \* \* \* \*

UNITED STATES PATENT AND TRADEMARK OFFICE
CERTIFICATE OF CORRECTION

PATENT NO. : 7,691,806 B2  Page 1 of 1
APPLICATION NO. : 11/351712
DATED : April 6, 2010
INVENTOR(S) : Katherine D. Collier et al.

It is certified that error appears in the above-identified patent and that said Letters Patent is hereby corrected as shown below:

Col 9, Line 51, "oleic acid)." should read as -- oleic acid. --

Col 10, Line 59, "amine oxides" should read as -- amine oxides. --

Col 21, Line 51, "CPB" should read as -- CBP --

Col 26, Line 43, "were also be" should read as -- were also --

Col 98, Line 28, "and a cater or" should read as -- and a carrier or --

Signed and Sealed this

Fourteenth Day of December, 2010

David J. Kappos
*Director of the United States Patent and Trademark Office*